US009439150B2

(12) United States Patent
Carlson et al.

(10) Patent No.: US 9,439,150 B2
(45) Date of Patent: Sep. 6, 2016

(54) CONTROL OF SPECTRAL AGRESSORS IN A PHYSIOLOGICAL SIGNAL MONTORING DEVICE

(71) Applicant: Medtronic, Inc., Minneapolis, MN (US)

(72) Inventors: David L. Carlson, Fridley, MN (US); Scott R. Stanslaski, Shoreview, MN (US); Peng Cong, Plymouth, MN (US); Timothy J. Denison, Minneapolis, MN (US); David E. Linde, Corcoran, MN (US); Randy M. Jensen, Hampton, MN (US)

(73) Assignee: Medtronic, Inc., Minneapolis, MN (US)

( * ) Notice: Subject to any disclaimer, the term of this patent is extended or adjusted under 35 U.S.C. 154(b) by 818 days.

(21) Appl. No.: 13/862,227

(22) Filed: Apr. 12, 2013

(65) Prior Publication Data
US 2014/0276185 A1 Sep. 18, 2014

Related U.S. Application Data

(60) Provisional application No. 61/799,674, filed on Mar. 15, 2013.

(51) Int. Cl.
*G06F 1/00* (2006.01)
*H04W 52/02* (2009.01)
(Continued)

(52) U.S. Cl.
CPC ...... *H04W 52/0238* (2013.01); *A61B 5/04004* (2013.01); *A61B 5/04012* (2013.01);
(Continued)

(58) Field of Classification Search
CPC ................ H04W 52/0238; A61B 5/04004; A61B 5/04012
See application file for complete search history.

(56) References Cited

U.S. PATENT DOCUMENTS

| 1,342,885 A | 6/1920 | Armstrong |
| 3,130,373 A | 4/1964 | Braymer |

(Continued)

FOREIGN PATENT DOCUMENTS

| EP | 0354060 A2 | 2/1990 |
| EP | 789449 A2 | 8/1997 |

(Continued)

OTHER PUBLICATIONS

Nielson et al., "A CMOS Low-Noise Instrumentation Amplifier Using Chopper Modulation," Analog Integrated Circuits and Signal Processing, vol. 42(1), Jan. 2005, pp. 65-76.
(Continued)

*Primary Examiner* — Jaweed A Abbaszadeh
*Assistant Examiner* — Austin Hicks
(74) *Attorney, Agent, or Firm* — Shumaker & Sieffert, P.A.

(57) ABSTRACT

This disclosure describes techniques for controlling spectral aggressors in a sensing device that uses a low power sleep mode to manage the power consumed by the device. In some examples, the techniques for controlling spectral aggressors may include configuring one or more of an algorithm processing rate for a processor, a buffering rate for the processor, a sampling rate for an analog-to-digital converter, an execution unit processing rate for the processor, and an algorithm subdivision factor for the processor such that spectral interference caused by a sleep cycle rate of the processor occurs outside of one or more target frequency bands of a sampled signal. The techniques of this disclosure may be used to reduce noise in a sensing system that uses a low power sleep mode to manage the power consumed by the device.

49 Claims, 7 Drawing Sheets

(51) Int. Cl.
  *A61B 5/00* (2006.01)
  *A61B 5/04* (2006.01)
  *G06F 1/32* (2006.01)

(52) U.S. Cl.
  CPC .......... *A61B5/7203* (2013.01); *A61B 5/7217* (2013.01); *A61B 5/7221* (2013.01); *A61B 5/7225* (2013.01); *G06F 1/3203* (2013.01); *H04W 52/028* (2013.01); *H04W 52/0274* (2013.01); *A61B 2560/0209* (2013.01)

(56) References Cited

U.S. PATENT DOCUMENTS

| | | |
|---|---|---|
| 4,138,649 A | 2/1979 | Schaffer |
| 4,177,819 A | 12/1979 | Kofsky et al. |
| 4,188,586 A | 2/1980 | Egami |
| 4,279,258 A | 7/1981 | John |
| 4,579,125 A | 4/1986 | Strobl et al. |
| 4,610,259 A | 9/1986 | Cohen et al. |
| 4,810,960 A | 3/1989 | Owen et al. |
| 4,933,642 A | 6/1990 | Lee |
| 4,979,230 A | 12/1990 | Marz |
| 5,061,593 A | 10/1991 | Yoerger et al. |
| 5,113,143 A | 5/1992 | Wei |
| 5,179,947 A | 1/1993 | Meyerson et al. |
| 5,206,602 A | 4/1993 | Baumgartner et al. |
| 5,311,876 A | 5/1994 | Olsen et al. |
| 5,458,117 A | 10/1995 | Chamoun et al. |
| 5,477,481 A | 12/1995 | Kerth |
| 5,619,536 A | 4/1997 | Gourgue |
| 5,663,680 A | 9/1997 | Nordeng |
| 5,725,558 A | 3/1998 | Warnke |
| 5,928,272 A | 7/1999 | Adkins et al. |
| 6,011,990 A | 1/2000 | Schultz et al. |
| 6,018,682 A | 1/2000 | Rise |
| 6,061,593 A | 5/2000 | Fischell et al. |
| 6,064,257 A | 5/2000 | Sauer |
| 6,129,681 A | 10/2000 | Kuroda et al. |
| 6,130,578 A | 10/2000 | Tang |
| 6,262,626 B1 | 7/2001 | Bakker et al. |
| 6,360,123 B1 | 3/2002 | Kimchi et al. |
| 6,456,159 B1 | 9/2002 | Brewer |
| 6,483,355 B1 | 11/2002 | Lee et al. |
| 6,584,351 B1 | 6/2003 | Ekwall |
| 6,617,838 B1 | 9/2003 | Miranda et al. |
| 6,625,436 B1 | 9/2003 | Tolson et al. |
| 6,667,760 B1 | 12/2003 | Limberg |
| 6,810,285 B2 | 10/2004 | Pless et al. |
| 6,876,842 B2 | 4/2005 | Davie |
| 6,993,380 B1 | 1/2006 | Modarres |
| 7,006,872 B2 | 2/2006 | Gielen et al. |
| 7,098,823 B2 | 8/2006 | O'Dowd et al. |
| 7,146,218 B2 | 12/2006 | Esteller et al. |
| 7,177,609 B1 | 2/2007 | Wong |
| 7,216,001 B2 | 5/2007 | Hacker et al. |
| 7,233,198 B2 | 6/2007 | Niederkorn |
| 7,385,443 B1 | 6/2008 | Denison |
| 7,391,257 B1 | 6/2008 | Denison et al. |
| 7,395,098 B2 | 7/2008 | Darabi |
| 7,622,988 B2 | 11/2009 | Denison et al. |
| 7,714,757 B2 | 5/2010 | Denison et al. |
| 7,847,628 B2 | 12/2010 | Denison |
| 8,099,073 B1 | 1/2012 | Muller et al. |
| 8,265,769 B2 | 9/2012 | Denison |
| 8,354,881 B2 | 1/2013 | Denison |
| 2003/0146786 A1 | 8/2003 | Gulati et al. |
| 2004/0002635 A1 | 1/2004 | Hargrove et al. |
| 2004/0077967 A1 | 4/2004 | Jordan |
| 2004/0141558 A1 | 7/2004 | Plisch et al. |
| 2004/0158119 A1 | 8/2004 | Osorio et al. |
| 2004/0167418 A1 | 8/2004 | Nguyen et al. |
| 2005/0081847 A1 | 4/2005 | Lee et al. |
| 2005/0118968 A1 | 6/2005 | Cowley |
| 2005/0226356 A1* | 10/2005 | Pirzada ............... G06F 11/00 375/350 |
| 2005/0282517 A1 | 12/2005 | Cowley |
| 2006/0055456 A1 | 3/2006 | Niederkorn |
| 2006/0133550 A1 | 6/2006 | Bolton et al. |
| 2006/0135877 A1 | 6/2006 | Giftakis et al. |
| 2006/0139192 A1 | 6/2006 | Morrow et al. |
| 2006/0139193 A1 | 6/2006 | Morrow et al. |
| 2006/0173501 A1 | 8/2006 | Stickney et al. |
| 2006/0281427 A1 | 12/2006 | Isaac et al. |
| 2006/0293720 A1 | 12/2006 | DiLorenzo |
| 2007/0010755 A1 | 1/2007 | Sarkela et al. |
| 2007/0032737 A1 | 2/2007 | Causevic et al. |
| 2007/0077907 A1 | 4/2007 | Rector |
| 2009/0082691 A1 | 3/2009 | Denison et al. |
| 2010/0327887 A1 | 12/2010 | Denison et al. |

FOREIGN PATENT DOCUMENTS

| | | |
|---|---|---|
| GB | 1249395 | 10/1971 |
| WO | WO 02/01711 | 1/2002 |
| WO | WO 02/03087 | 1/2002 |
| WO | WO 2006/066098 A1 | 6/2006 |

OTHER PUBLICATIONS

Rudell et al., "Recent developments in high integration multi standard CMOS transceivers for personal communication systems," Proceedings. 1998 International Symposium on Low Power Electronics and Design, The Association for Computing Machinery, Inc. (ACM), 1998, pp. 149-154, 6 pp.

"Baseband" entry, Academic Press Dictionary of Science and Technology, Oxford: Elsevier Science and Technology, 1992, 2 pp.

"Baseband" entry and p. 86, Authoritative Dictionary of IEEE Standard Terms (Seventh Edition), New York: IEEE, 2000, 3 pp. w York, 2000, 3 pp.

International Search Report and Written Opinion of Corresponding International Application No. PCT/US2014/021692, dated May 22, 2014, 10 pp.

Abidi, "CMOS Wireless Transceivers: the new wave," IEEE Communications Magazine, Aug. 1999, pp. 119-124.

Anderson et al., "Recording Advances for Neural Prosthetics," in Engineering in Medicine and Biology Society, Sep. 2004, 26th Annual International Conference of the IEEE, pp. 5352-5355, vol. 7.

Anderson et al., "Selecting the signals for a brain-machine interface," Curr Opin Neurobiol, vol. 14, pp. 720-726, Dec. 2004.

Bakker et al., "A CMOS Nested-Chopper Instrumentation Amplifier with 100-nV Offset," IEEE Journal of Solid-State Circuits, vol. 35, No. 12, pp. 1877-1883, Dec. 2000.

Boser, "Capacitive Interfaces for Monolithic Integrated Sensors," Chapter in "RF Analog-to-Digital Converters; Sensor and Actuator Interfaces; Low-Noise Oscillators, PLLs and Synthesizers," R.J. van de Plaasche, J.H. Huijsing, and W.M.C. Sansen (eds.), Kluwer Academic Publishers, Nov. 1997, 20 pp.

Burt et al., "A Micropower Chopper-Stabilized Operational Amplifier using an SC Notch Filter with Synchronous Integration inside the Continuous-Time Signal Path," ISSCC Digest of Technical Papers 2006, paper 19.6, Feb. 2006, 2 pp.

Denison et al., "A 2.2µ W 94nV/√Hz, Chopper-Stabilized Instrumentation Amplifier for EEG Detection in Chronic Implants" JSSC, vol. 42, No. 12, pp. 2934-2945, Dec. 2007.

Denison et al., "A 2µ W 100 nV/rtHz Chopper-Stabilized Instrumentation Amplifier for Chronic Measurement of Neural Field Potentials," Solid-state circuits, IEEE Journal, vol. 42, pp. 2934-2945, Dec. 2007.

Denison et al., "An 8µ W heterodyning chopper amplifier for direct extraction of 2µVrms Neuronal Brain Biomarkers," ISSCC, Jul. 2008, paper 8.1, 3 pp.

Enz et al., "Circuit Techniques for Reducing the Effects of Op-Amp Imperfections: Autozeroing, Correlated Double Sampling, and Chopper Stabilization," Proc. of the IEEE, vol. 84, No. 11, pp. 1584-1614, Nov. 1996.

Haddad et al., "An ultra low-power dynamic translinear cardiac sense amplifier for pacemakers," Circuits and Systems, Mar. 2003, pp. V-37-V40, vol. 5.

(56) References Cited

OTHER PUBLICATIONS

Haddad et al., "Analog wavelet transform employing dynamic translinear circuits for cardiac signal characterization," Circuits and Systems, 2003, pp. 1-121-1-124, vol. 1.
Hadiashar et al., "A Chopper Stabilized CMOS Analog Multiplier with Ultra Low DC Offsets," Solid-State Circuits Conference, pp. 364-367, Sep. 2006.
Harrison et al., "A Low-Power Low-Noise CMOS Amplifier for Neural Recording Applications," IEEE J. of Solid-State Circuits, vol. 38, No. 6, pp. 958-965, Jun. 2003.
Harrison et al., "Local Field Potential Measurement with Low-Power Analog Integrated Circuit," Sep. 1-5, 2004, 4 pp.
Harrison et al., A Low-Power Integrated Circuit for a Wireless 100—Electrode Neural Recording System, Solid state circuits. IEEE Journal of, vol. 42, pp. 123-133, Jan. 2007.
Krusienski et al.,"A μ-Rhythm Matched Filter for Continuous Control of a Brain-Computer Interface," Biomedical Engineering, IEEE Transactions on, vol. 54, pp. 273-280, Feb. 2007.
Lee et al., "A 64 Channel Programmable Closed-Loop Deep Brain Stimulator with 8 channel Neural Amplifier and Logarithmic ADC," 2008 Symposium on VLSI Circuits Digest of Technical Papers, pp. 76-77, Mar. 2008.
Makinwa et al., A CMOS Temperature-to-frequency converter with an Inaccuracy of less than ±0.5 ° C. (3σ) from -40 ° C. to 105 ° C., IEEE Journal of Solid State Circuits, vol. 41, No. 12 , pp. 2992-2997, Dec. 2006.
Makinwa, "Dynamic Offset Cancellation Techniques," Smart Sensor Systems '02, May 2002, 42 pp.
Martins et al., "A CMOS IC for Portable EEG Acquisition Systems," IEEE Transactions on Instrumentation and Measurement, vol. 47, No. 5, pp. 1191-1196, Oct. 1998.
Ng et al., "A CMOS Analog Front-End IC for Portable EEG/ECG Monitoring Applications," IEEE Trans. on Circuits and Systems, vol. 52 No. 11, Nov. 2005, 13 pp.
Rauscher, "Practical Realization of an Analyzer Operating on the Heterodyne Principle," part of Chapter 4 of Fundamentals of Spectrum Analysis (Rohe & Schwarz), 2001, 35 pp.
Salthouse et al., "A practical micropower programmable bandpass filter for use in bionic ears," Solid-state Circuits, IEEE Journal, vol. 38, pp. 63-70, Jan. 2003.
Sanduleanu et al., "A Low Noise, Low Residual Offset, Chopped Amplifier for Mixed Level Applications," IEEE, pp. 333-336, Sep. 1998.
Sarpeshkar et al., "An ultra-low-power programmable analog bionic ear processor," Biomedical Engineering, IEEE Transactions, vol. 52, pp. 711-727, Apr. 2005.
Sarpeshkar et al., Low power circuits for brain -machine interfaces, Circuits and Systems, Sep. 2007, pp. 2068-2071.
Sarpeshkar, "Borrowing from biology makes for low-power computing," IEEE Spectrum, pp. 24-29, May 2006.
Smart et al., "Automatic Detection of High Frequency Epileptiform Oscillations from Intracranial EEG Recordings of Patients with Neocortical Epilepsy," in Technical, Professional and Student Development Workshop, 2005 IEEE Region 5 and IEEE Denver Section, Apr. 2005, pp. 53-58.
Wattanapanitch et al., "An energy-efficient micropower neural recording amplifier," Biomedical Circuits and Systems, IEEE Transactions, vol. 1, No. 2, pp. 136-147, Jun. 2007.
Wu et al., "A 1V 2.3 1μ W Biomedical Signal Acquisition IC," ISSCC Digest of Technical Papers 2006, paper 2.7, Feb. 2006, 2 pp.
Yates et al., "An Ultra Low Power Noise Chopper Amplifier for Wireless EEG," 49th IEEE International Midwest Symposium on Circuits and Systems, 2006, vol. 2, pp. 449-452.
Yazicioglu et al., "A 200μ W Eight-Channel Acquisition ASIC for Ambulatory EEG Systems," Solid-state circuits conference, Jul. 2008, 3 pp.
Yazicioglu et al., "A 60μ W 60nV/√Hz Readout Front-End for Portable Biopotential Acquisition Systems," ISSCC Digest of Technical Papers 2006, paper 2.6, Feb. 2006, 2 pp.
Ying, "Chopper Stabilized Amplifiers," Term Paper, Department of Electrical and Computer Engineering, University of Toronto, 17 pp., Nov. 12, 2001.
U.S. Appl. No. 13/862,238, by Scott R. Stanslaski, filed Apr. 12, 2013.

* cited by examiner

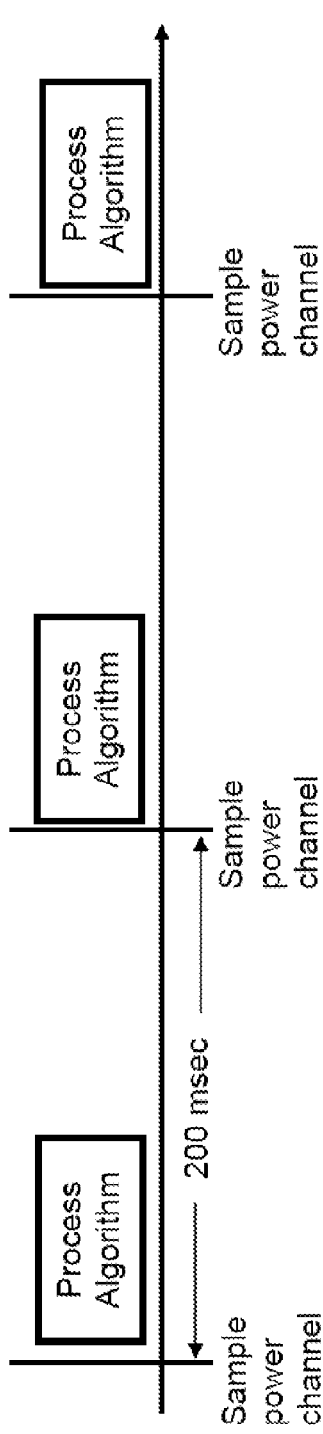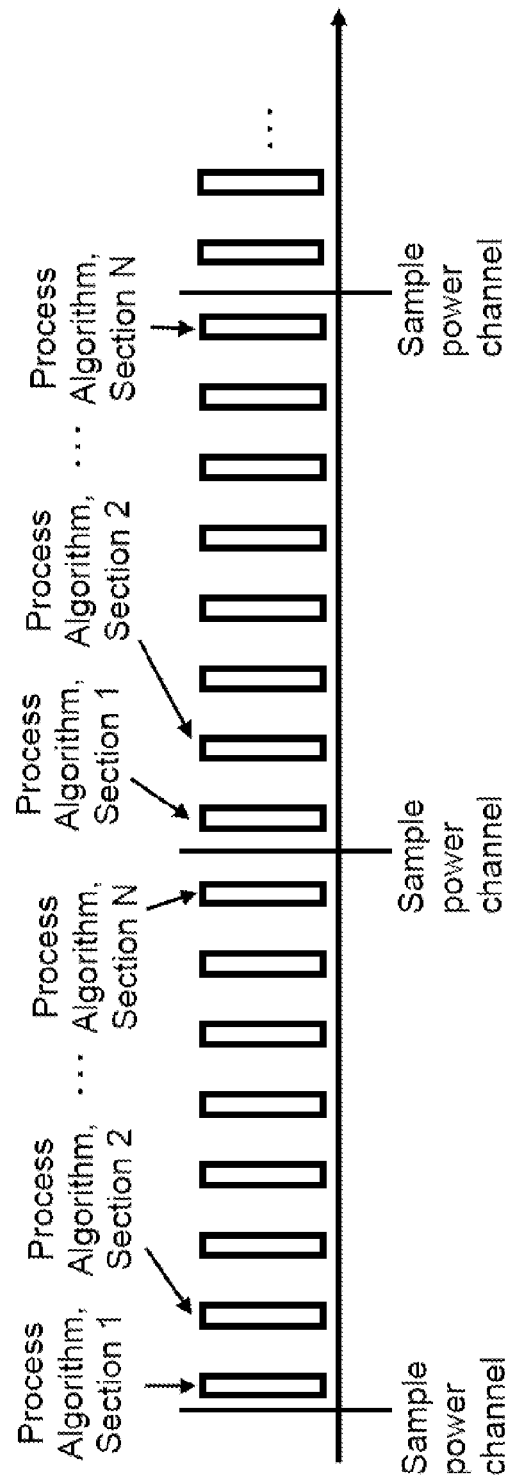

CONTROL OF SPECTRAL AGRESSORS IN A PHYSIOLOGICAL SIGNAL MONTORING DEVICE

This application claims the benefit of U.S. Provisional Application No. 61/799,674, filed Mar. 15, 2013, the entire content of which is incorporated herein by reference.

TECHNICAL FIELD

This disclosure relates to medical devices and, more particularly, to the monitoring of physiological signals with a medical device.

BACKGROUND

Medical devices may be used to deliver therapy to patients to treat a variety of symptoms or conditions. Examples of therapy include electrical stimulation therapy and drug delivery therapy. Examples of symptoms or conditions include chronic pain, tremor, akinesia, Parkinson's disease, epilepsy, dystonia, neuralgia, obsessive compulsive disorder (OCD), depression, sleep dysfunction, urinary or fecal incontinence, sexual dysfunction, obesity, or gastroparesis. Information relating to symptoms or conditions may be sensed by monitoring physiological signals, such as, e.g., electrocardiogram (ECG) signals, electromyogram (EMG) signals, electroencephalogram (EEG) signals, electrocorticogram (ECoG) signals, pressure signals, temperature signals, impedance signals, motion signals, and other types of signals. In some cases, the physiological signals associated with a patient may be relatively low voltage signals that have information encoded at relatively low frequencies in the signal, such as, e.g., brain signals. Detecting information in low voltage and low frequency signals may present significant challenges in medical devices, particularly in the case of implantable medical devices where power resources may be limited.

SUMMARY

This disclosure describes techniques for controlling spectral aggressors in a sensing device that uses a low power sleep mode to manage the power consumed by the device. In some examples, the techniques for controlling spectral aggressors may include configuring the sleep cycle rate of a processor that processes sensed signals such that the sleep cycle rate causes spectral interference that is generated due to the sleep cycle rate to occur in a sampled signal at one or more frequencies that are outside of the target frequency band of the sampled signal. In some examples, one or more of an algorithm processing rate, a buffering rate, a sampling rate, an execution unit processing rate, and an algorithm subdivision factor may be configured to achieve a particular sleep cycle rate.

In one example, this disclosure describes a signal monitoring device that includes a power source and a power distribution network electrically coupled to the power source. The device further includes an analog-to-digital converter electrically coupled to the power distribution network and configured to sample an input signal to produce a sampled signal. The device further includes a processor electrically coupled to the power distribution network and configured to cycle between an algorithm processing mode and a sleep mode based on a sleep cycle rate. The sleep cycle rate causes spectral interference to propagate through the power distribution network and into the sampled signal via the analog-to-digital converter. The sleep cycle rate further causes the spectral interference that is generated due to the sleep cycle rate to occur in the sampled signal at one or more frequencies that are outside of a target frequency band of the sampled signal.

In another example, this disclosure describes a method for monitoring a signal. The method includes sampling, with an analog-to-digital converter, an input signal to produce a sampled signal. The method further includes cycling a processor between an algorithm processing mode and a sleep mode based on a sleep cycle rate. The analog-to-digital converter and the processor are both electrically coupled to a power distribution network that is electrically coupled to a power source. The sleep cycle rate causes spectral interference to propagate through the power distribution network and into the sampled signal via the analog-to-digital converter. The sleep cycle rate further causes the spectral interference that is generated due to the sleep cycle rate to occur in the sampled signal at one or more frequencies that are outside of a target frequency band of the sampled signal.

In another example, this disclosure describes an apparatus for monitoring a signal. The apparatus includes means for sampling an input signal to produce a sampled signal. The apparatus further includes means for cycling between an algorithm processing mode and a sleep mode based on a sleep cycle rate. The means for sampling and the means for cycling are electrically coupled to a power distribution network that is electrically coupled to a power source. The sleep cycle rate causes spectral interference to propagate through the power distribution network and into the sampled signal. The sleep cycle rate further causes the spectral interference that is generated due to the sleep cycle rate to occur in the sampled signal at one or more frequencies that are outside of a target frequency band of the sampled signal.

The details of one or more examples of the disclosure are set forth in the accompanying drawings and the description below. Other features, objects, and advantages of the disclosure will be apparent from the description and drawings, and from the claims.

BRIEF DESCRIPTION OF DRAWINGS

FIGS. 5A and 5B are conceptual diagrams illustrating an example of how the algorithm subdivision techniques described in this disclosure may be used to move spectral aggressors out of a target frequency band of interest.

DETAILED DESCRIPTION

Figure 1:
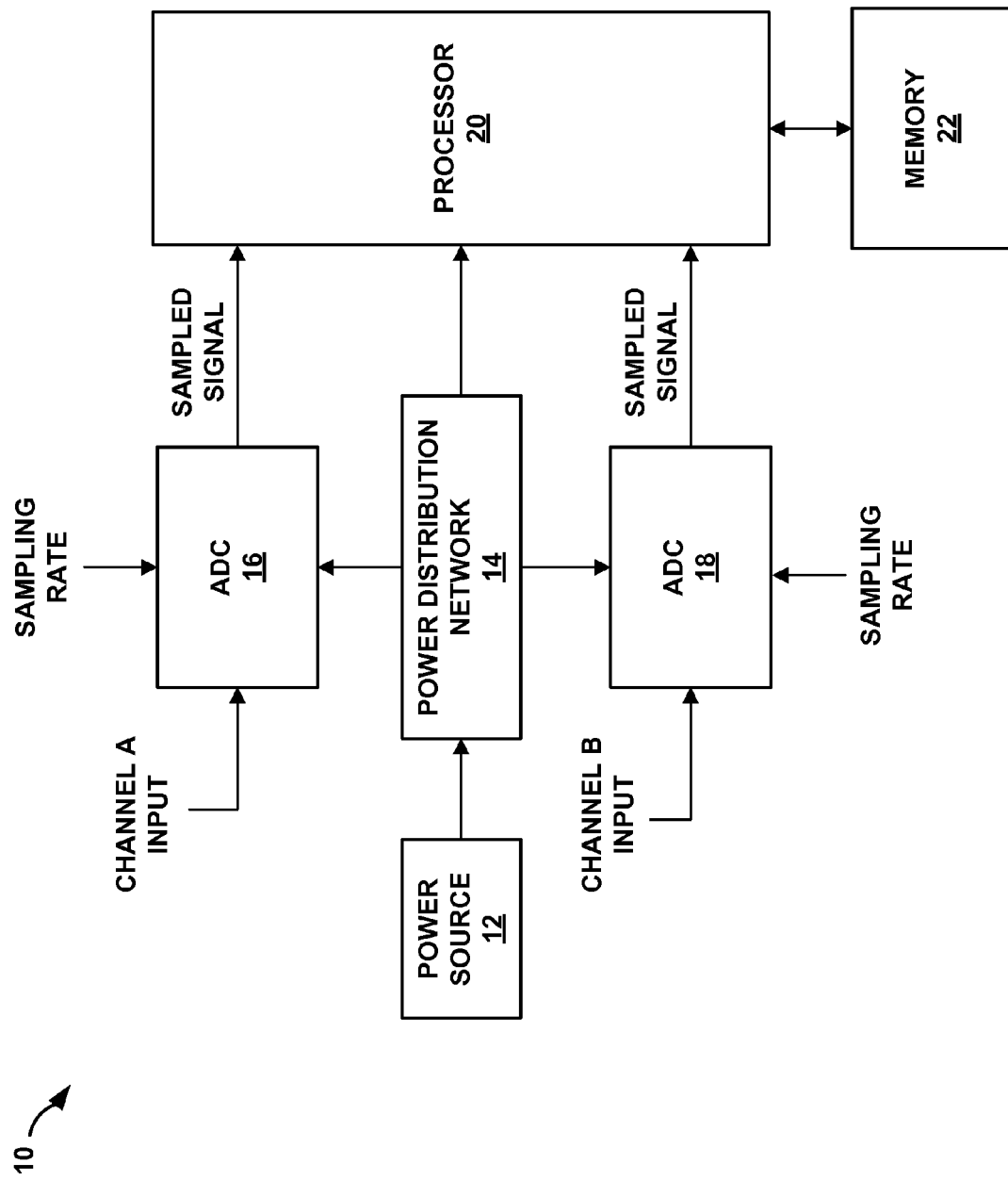
FIG. 1 is a block diagram illustrating example sensing and analysis circuitry that may be used to perform the spectral aggressor control techniques of this disclosure.

This disclosure describes techniques for controlling spectral aggressors in a sensing device that uses a low power sleep mode to manage the power consumed by the device. In some examples, the techniques for controlling spectral aggressors may include configuring the sleep cycle rate of a processor that processes sensed signals such that the sleep cycle rate causes spectral interference that is generated due to the sleep cycle rate to occur in a sampled signal at one or more frequencies that are outside of the target frequency band of the sampled signal. In some examples, one or more of an algorithm processing rate, a buffering rate, a sampling rate, an execution unit processing rate, and an algorithm subdivision factor may be configured to achieve a particular sleep cycle rate.

Sensing devices may use a digital microprocessor to analyze sensed signals and/or to store sensed signals into a memory. An analog-to-digital converter (ADC) may be used to generate sampled signals that may be further processed by the digital processor. In some cases, the digital processor may be able to process a sampled signal at a rate that is faster than the rate at which the signal is sampled. In order to save power in such situations, when the processing algorithms performed by the processor have completed execution for a particular set of data samples, the digital processor may enter a low-power sleep mode until the next set of data samples is received. Transitioning into and out of the low-power sleep mode may cause significant fluctuations in the current drain from a power source that powers the digital processor, particularly in applications where power is limited, such as, e.g., in an implantable medical device.

In some sensing devices, the ADC circuits and the digital processor may be electrically coupled to a common power source via a common power distribution network. In such devices, the current fluctuations caused in the power distribution network by the sleep mode cycling may propagate into the ADC circuits and introduce one or more spectral aggressors into one or more of the sampled signals produced by the ADC circuits. In some cases, the spectral aggressors may be positioned in a target frequency band of interest in one or more of the sampled signals resulting in unwanted spectral noise.

The techniques of this disclosure may control spectral aggressors that are caused by the sleep mode cycling of a processor such that the spectral aggressors occur outside of a target frequency band of interest in a sampled signal. In some examples, the spectral aggressor control techniques of this disclosure may include configuring the sleep cycle rate of a processor that analyzes sensed signals such that the sleep cycle rate causes spectral interference that is generated due to the sleep cycle rate to occur in a sampled signal at one or more frequencies that are outside of the target frequency band of the sampled signal. In some examples, one or more of an algorithm processing rate, a buffering rate, a sampling rate, an execution unit processing rate, and an algorithm subdivision factor may be configured to achieve a particular sleep cycle rate. Moving spectral aggressors that are caused by the sleep mode cycling of a processor to portions of the sampled signal that are outside of the target frequency band of interest may reduce the amount of noise in the target frequency band of the sampled signal, thereby improving the ability of a signal monitoring device to analyze one or more characteristics of the target frequency band.

In some examples, the algorithm processing rate (e.g., the rate at which the digital processor invokes a processing algorithm) may be configured such that the spectral interference caused by the sleep cycle rate occurs in the sampled signal at the one or more frequencies that are outside of the target frequency band of the sampled signal. In some cases, the algorithm processing rate may correspond to the sampling rate. In such examples, the sampling rate may be configured such that the spectral interference caused by the sleep cycle rate occurs in the sampled signal at one or more frequencies that are outside of the target frequency band of a sampled signal.

In further examples, a processing algorithm that is executed by the digital processor may be invoked with respect to multiple data samples, and the processor may buffer the data samples prior to invoking the processing algorithm. In such examples, the algorithm processing rate may be dependent upon the sampling rate and the buffering rate. To control the spectral aggressors in such examples, one or both of the sampling rate and the buffering rate may be configured such that the spectral interference caused by the sleep cycle rate occurs in the sampled signal at one or more frequencies that are outside of the target frequency band of the sampled signal.

In additional examples, the execution of a single instance of a processing algorithm may be subdivided into multiple smaller execution units. These execution units may be executed by the processor during separate time intervals. In such examples, the rate at which each subdivided portion of the algorithm is processed may be dependent on the algorithm processing rate for the entire algorithm and an algorithm subdivision factor. To control the spectral aggressors in such examples, one or both of the algorithm processing rate and the algorithm subdivision factor may be configured such that the spectral interference caused by the sleep cycle rate occurs in the sampled signal at one or more frequencies that are outside of the target frequency band of the sampled signal.

In some examples, both buffering and algorithm subdivision may be used in a sensing system. In such examples, the rate at which each subdivided portion of the algorithm is processed may be dependent on the buffering rate, the sampling rate, and the algorithm subdivision factor. To control the spectral aggressors in such examples, one or more of the buffering rate, the sampling rate, and the algorithm subdivision factor may be configured such that the spectral interference caused by the sleep cycle rate occurs in the sampled signal at one or more frequencies that are outside of the target frequency band of the sampled signal.

In some examples, the techniques of this disclosure may be used to sense, monitor, and analyze brain signals, such as, e.g., EEG signals, ECoG signals, and local field potentials (LFP's). Brain signals may include neurological biomarkers that are encoded as power fluctuations in particular frequency bands of the brain signal. For example, visual processing and motor planning may be correlated with power fluctuations in the alpha band (e.g., 5 to 15 Hz), and the symptoms of Parkinson's disease may be correlated with power fluctuations in the beta band (e.g., 15 to 35 Hz). Other target frequency bands of interest for the brain signal may include the delta band (e.g., 1 Hz or lower), the theta band (e.g., 4 to 8 Hz), and the gamma band (e.g., 30-100 Hz).

In some cases, a device that is configured to sense brain signals may include multiple channels with one or more of the channels each being configured to convert a particular target frequency band of the brain signal to baseband for sensing and one or more of the channels each being configured to sense a wide-band time-domain version of the brain signal. Because of the relatively low frequencies of interest in the brain signals, the sampling rate for the digital processor may also be relatively low. However, if the different channels are powered by a common power source and if sleep cycling is used to manage power consumption in the device, then the spectral aggressors from one channel may interfere with the signals in other channels such as, e.g., the time domain channel. The techniques of this disclosure may be used to move spectral aggressors caused by one channel out of a target frequency band of interest that is located in the same channel or in another channel. In this way, the power savings provided by a sleep cycling processor may be leveraged while ensuring that any spectral aggressors caused by the sleep cycling of the processor do not interfere with the target frequency band of interest that is to be analyzed.

FIG. 1 is a block diagram illustrating example sensing and analysis circuitry 10 that may be used to perform the spectral aggressor control techniques of this disclosure. Sensing and analysis circuitry 10 is configured to sense and analyze an input signal received from one or more sensing elements. In some examples, the input signal may be a physiological signal received from one or more sensing elements (e.g., electrodes) that are attached to, proximate to, and/or implanted within a human being. Sensing and analysis circuitry 10 includes a power source 12, a power distribution network 14, analog-to-digital converters (ADCs) 16, 18, a processor 20, and a memory 22.

Power source 12 may provide power to ADCs 16, 18 and processor 20 via power distribution network 14. In some cases, power source 12 may also provide power to memory 22. Power source 12 may be any type of power source, including, but not limited to, a battery power source (e.g., a rechargeable or nonrechargeable battery), a charged capacitor power supply, a voltage multiplier power supply, a direct current (DC) power supply, an alternating current (AC) power supply, etc.

Power distribution network 14 distributes power from power source 12 to ADCs 16, 18 and processor 20. Power distribution network 14 may be any type of power distribution system including, but not limited to, conductive traces, wires, etc. Power distribution network 14 is electrically coupled to power source 12, ADCs 16, 18, and processor 20.

Each of ADCs 16, 18 is configured to receive a respective one of the input signals, and to sample the respective one of the input signals at a respective sampling rate to generate a sampled signal. Sampling a signal may refer to the process of converting a continuous-time signal to a discrete-time signal. A sampling rate may refer to the rate or frequency at which samples of the continuous-time signal are taken. The sampling rate may alternatively be referred to as a sampling frequency. In some examples, ADCs 16, 18 may also quantize the input signals to produce the sampled signals. In such examples, the sampled signals may correspond to digital signals.

As shown in FIG. 1, each of ADCs 16, 18 may form a separate sensing channel. For example, ADC 16 may sense an input signal for channel A, and ADC 18 may sense an input signal for channel B. ADCs 16, 18 are electrically coupled to power distribution network 14 and to power source 12 via power distribution network 14.

Processor 20 may be configured to analyze information contained in one or more target frequency bands of the sampled signals produced by one or both of ADCs 16, 18 and/or to store data samples associated with the sampled signals produced by one or both of ADCs 16, 18 into memory 22. In some examples, processor 20 may determine a power level of a target frequency band in one or both of the sampled signals. In further examples, processor 20 may determine a power fluctuation of a target frequency band in one or both of the sampled signals.

To analyze the information contained in a target frequency band and/or to store the data samples into memory 22, processor 20 may, in some examples, execute one or more processing algorithms for a set of one or more data samples received by one or both of ADCs 16, 18. In some examples, one or more of the processing algorithms may analyze a target frequency band of interest. The target frequency band of interest analyzed by each of the algorithms may be the same or different. In further examples, one or more of the processing algorithms may store the data samples into memory 22. In such examples, the data samples may be subsequently retrieved by processor 20 or another processor for further analysis in the target frequency band of interest.

Processor 20 may be implemented as one or more digital processors, microprocessors, digital signal processors (DSPs), application specific integrated circuits (ASICs), field programmable logic arrays (FPGAs), etc. Processor 20 is electrically coupled to power distribution network 14 and to power source 12 via power distribution network 14.

Memory 22 may be configured to store data samples for subsequent retrieval by processor 20 or another processor. Memory 22 may include any combination of volatile, non-volatile, removable, magnetic, optical, or solid state media, such as read-only memory (ROM), random access memory (RAM), electronically-erasable programmable ROM (EEPROM), flash memory, or the like.

During operation, processor 20 may execute one or more processing algorithms at an algorithm processing rate. The algorithm processing rate may refer to the rate at which instances of the algorithm are invoked by processor 20.

In some examples, processor 20 may invoke an instance of the processing algorithm for every data sample received by processor 20 from ADCs 16, 18. In such examples, the algorithm processing rate may correspond to the sampling rate of one or both of ADCs 16, 18.

In further examples, processor 20 may invoke an instance of the processing algorithm for every set of multiple data samples that are received by processor 20 from ADCs 16, 18. In such examples, processor 20 may buffer the data samples to be used for a single invocation of the algorithm prior to invoking the processing algorithm. The number of data samples to be buffered per invocation of the processing algorithm may be referred to as the buffering rate. In such examples, the algorithm processing rate may correspond to a quotient of the sampling rate divided by the buffering rate.

In additional examples, processor 20 may subdivide the execution of a single instance of a processing algorithm into multiple smaller execution units, and may execute the smaller execution units during separate time intervals. For example, processor 20 may execute the execution units of the processing algorithm at an execution unit processing rate. The execution unit processing rate may refer to the rate at which individual execution units of an instance of an algorithm are processed. The execution unit processing rate may be equal to the product of the algorithm processing rate and an algorithm subdivision factor. The algorithm subdivision factor may specify the number of separate execution units (e.g., processing portions) into which a single invocation of a processing algorithm is subdivided. The algorithm subdivision factor may also specify the number of separate time intervals that are to be used for execution a single invocation of the processing algorithm.

Processor 20 may be configured to operate in an algorithm processing mode and a sleep mode. When operating in the algorithm processing mode, processor 20 may be configured to execute one or more portions of a processing algorithm. When operating in the sleep mode, processor 20 may not execute any processing algorithms. When operating in the sleep mode, processor 20 may consume less power than when operating in the algorithm processing mode. As such, the sleep mode may be referred to as a low-power sleep mode.

In cases where processor 20 does not subdivide the processing algorithm into execution units, processor 20 may be configured to enter the sleep mode between each invocation of a processing algorithm. In other words, processor 20 may transition to the sleep mode after an instance of the processing algorithm has completed execution, and may transition to the algorithm processing mode in response to the execution of a subsequent instance of the processing algorithm being invoked.

In cases where processor 20 subdivides the processing algorithm into execution units, processor 20 may be configured to enter the sleep mode between the execution of each of the execution units of the processing algorithm. In other words, processor 20 may transition to the sleep mode after an execution unit of the processing algorithm has completed execution, and may transition to the algorithm processing mode in response to encountering a time interval at which a subsequent execution unit is to be processed.

Because processor 20 may receive and process data samples at regular intervals, the entering and exiting of the sleep mode by processor 20 may occur at regular, periodic intervals. The rate at which processor 20 transitions into and/or out of the sleep cycle mode may be referred to herein as the sleep cycle rate. Transitioning into and out of the low-power sleep mode may cause significant fluctuations in the current drain from power source 12. The current fluctuations may propagate through power distribution network 14 and into ADCs 16, 18, thereby introducing one or more spectral aggressors into one or more of the sampled signals produced by ADCs 16, 18. The frequencies of the one or more spectral aggressors may correspond to, be related to, and/or be equal to the sleep cycle rate.

According to this disclosure, one or more of the algorithm processing rate for processor 20, the buffering rate for processor 20, the sampling rate for ADCs 16, 18, the execution unit processing rate for processor 20, and the algorithm subdivision factor for processor 20 may be configured such that spectral interference caused by the sleep cycle rate occurs in one or both of the sampled signals produced by ADCs 16, 18 at one or more frequencies that are outside of one or more target frequency bands of the sampled signals. Moving spectral aggressors that are caused by the sleep mode cycling of processor 20 to portions of the sampled signal that are outside of the target frequency band of interest may reduce the amount of noise in the target frequency band of the sampled signal, thereby improving the ability of sensing and analysis circuitry 10 to analyze one or more characteristics of the target frequency band of the sampled signal and/or to perform post-processing of recorded data.

In some examples, ADC 16 may sample an input signal in Channel A to produce a sampled signal. In such examples, processor 20 may cycle between an algorithm processing mode and a sleep mode based on a sleep cycle rate, and in some cases, analyze a target frequency band of the sampled signal. The sleep cycle rate may cause spectral interference to propagate through power distribution network 14 and into the sampled signal via ADC 16. The sleep cycle rate may further cause spectral interference that is generated due to the sleep cycle rate to occur in the sampled signal generated by ADC 16 at one or more frequencies that are outside of the target frequency band of the sampled signal.

In further examples, the sleep cycle rate for processor 20 may be configured such that the spectral interference caused by the sleep cycle rate occurs in the sampled signal generated by ADC 16 at one or more frequencies that are outside of the target frequency band of the sampled signal. For example, the sleep cycle rate may be configured such that the sleep cycle rate is greater than an upper bound frequency of the target frequency band of the sampled signal generated by ADC 16. As another example, the sleep cycle rate may be configured such that the sleep cycle rate is less than a lower bound frequency of the target frequency band of the sampled signal generated by ADC 16.

In additional examples, processor 20 may invoke instances of a processing algorithm at an algorithm processing rate to process the sampled signal generated by ADC 16. In such examples, the sleep cycle rate may be configured to be equal to the algorithm processing rate, and the algorithm processing rate may be configured such that the spectral interference caused by the sleep cycle rate occurs in the sampled signal generated by ADC 16 at one or more frequencies that are outside of the target frequency band of the sampled signal.

In some examples, ADC 18 may sample a channel B input signal to produce a sampled signal, and processor 20 may invoke instances of a processing algorithm at an algorithm processing rate to process the sampled signal generated by ADC 18. In such examples, the sleep cycle rate may be equal to the algorithm processing rate, and the algorithm processing rate may be configured such that spectral interference caused by the sleep cycle rate occurs in a sampled signal generated by ADC 16 at one or more frequencies that are outside of the target frequency band of the sampled signal generated by ADC 16.

In further examples, ADC 16 may sample the input signal at a sampling rate, and processor 20 may buffer the sampled signal at a buffering rate and invoke instances of the processing algorithm at a rate equal to a quotient of the sampling rate divided by the buffering rate to process the sampled signal. The buffering rate may be indicative of a number of data samples to buffer per invocation of a processing algorithm. In such examples, the sleep cycle rate may be configured to be equal to the quotient of the sampling rate divided by the buffering rate, and the buffering rate and the sampling rate may be configured such that the spectral interference caused by the sleep cycle rate occurs in the sampled signal generated by ADC 16 at one or more frequencies that are outside of the target frequency band of the sampled signal generated by ADC 16.

In additional examples, ADC 18 may sample a channel B input signal at a sampling rate to produce a sampled signal, processor 20 may buffer the sampled signal generated by ADC 18 at a buffering rate and invoke instances of the processing algorithm at a rate equal to a quotient of the sampling rate divided by the buffering rate to process the sampled signal generated by ADC 18. In such examples, the sleep cycle rate may be configured to be equal to the quotient of the sampling rate divided by the buffering rate. Also in such examples, the buffering rate and the sampling rate may be configured such that spectral interference caused by the sleep cycle rate occurs in a sampled signal generated by ADC 16 at one or more frequencies that are outside of the target frequency band of the sampled signal generated by ADC 16.

In yet further examples, processor 20 may invoke instances of a processing algorithm at an algorithm processing rate to process the sampled signal generated by ADC 16. For each of the instances of the processing algorithm that are invoked, processor 20 may execute the respective instance of the processing algorithm during a number of separate time intervals. Each of the separate time intervals may be separated from adjacent time intervals by a time interval where the respective processing algorithm is not executed by processor 20. The number of separate time intervals may be determined by an algorithm subdivision factor. In such examples, the sleep cycle rate may be configured to be equal to a product of an algorithm processing rate and the algorithm subdivision factor, and the algorithm processing rate and the algorithm subdivision factor may be configured such that spectral interference caused by the sleep cycle rate occurs in the sampled signal generated by ADC 16 at the one or more frequencies that are outside of the target frequency band of the sampled signal generated by ADC 16.

In some implementations of the previous example, ADC 16 may sample the input signal at a sampling rate to produce a sampled signal, and processor 20 may buffer the sampled signal at a buffering rate. In such implementations, the algorithm processing rate may be equal to a quotient of the sampling rate divided by the buffering rate. Also in such implementations, the sampling rate, the buffering rate and the algorithm subdivision factor may be configured such that the spectral interference caused by the sleep cycle rate occurs in the sampled signal generated by ADC 16 at one or more frequencies that are outside of the target frequency band of the sampled signal generated by ADC 16.

In additional examples, ADC 18 may sample a channel B input signal to produce a sampled signal, and processor 20 may invoke instances of a processing algorithm at an algorithm processing rate to process the sampled signal generated by ADC 18. For each of the instances of the processing algorithm that are invoked, processor 20 may execute the respective instance of the processing algorithm during a number of separate time intervals. The number of separate time intervals may be determined by an algorithm subdivision factor. In such examples, the sleep cycle rate may be configured to be equal to a product of the algorithm processing rate and the algorithm subdivision factor. Also in such examples, the algorithm processing rate and the algorithm subdivision factor may be configured such that the spectral interference caused by the sleep cycle rate occurs in a sampled signal generated by ADC 16 at one or more frequencies that are outside of the target frequency band of the sampled signal generated by ADC 16.

In some implementations of the previous example, ADC 18 may sample the channel B input signal at a sampling rate to produce a sampled signal, and processor 20 may buffer the sampled signal generated by ADC 18 at a buffering rate. The buffering rate may be indicative of a number of data samples to buffer per invocation of the processing algorithm. In such examples, the algorithm processing rate may be equal to a quotient of the sampling rate divided by the buffering rate. Also in such examples, the sampling rate, the buffering rate and the algorithm subdivision factor may be configured such that the spectral interference caused by the sleep cycle rate occurs in the sampled signal generated by ADC 16 at the one or more frequencies that are outside of the target frequency band of the sampled signal generated by ADC 16.

Figure 2:
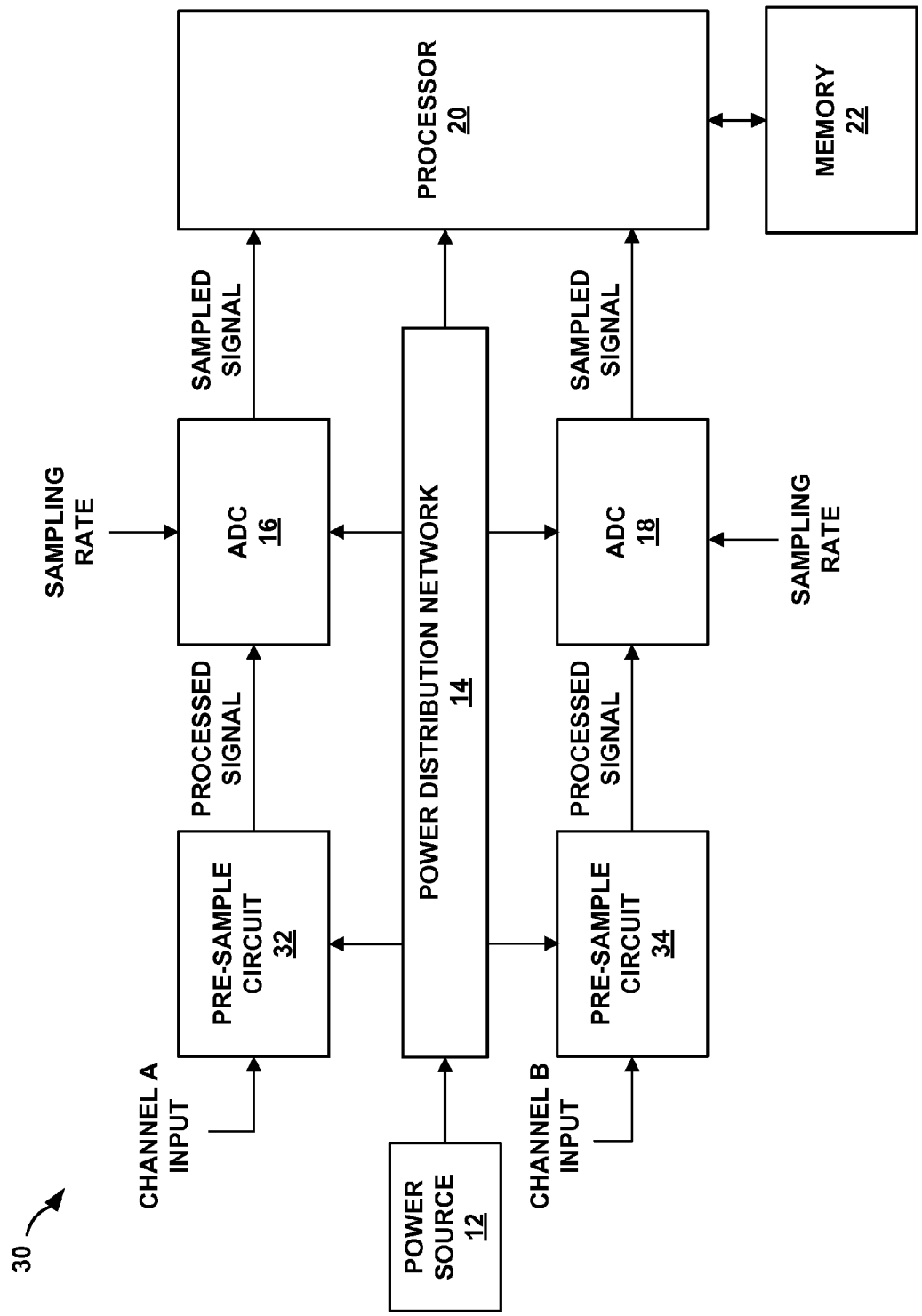
FIG. 2 is a block diagram illustrating another example sensing and analysis circuitry that may be used to perform the spectral aggressor control techniques of this disclosure.

FIG. 2 is a block diagram illustrating another example sensing and analysis circuitry 30 that may be used to perform the spectral aggressor control techniques of this disclosure. The sensing and analysis circuitry 30 illustrated in FIG. 2 is substantially similar to the sensing and analysis circuitry 10 illustrated in FIG. 1, except that sensing and analysis circuitry 30 includes additional pre-sample circuits 32, 34 that process the Channel A and Channel B input signals, respectively, prior to being received by ADCs 16, 18, respectively. As shown in FIG. 2, pre-sample circuit 32 and ADC 16 may form a first sensing channel (i.e., Channel A), and pre-sample circuit 34 and ADC 18 may form a second sensing channel (i.e., Channel B).

In some examples, one or both of pre-sample circuits 32, 34 may amplify the input signal to produce an amplified signal. In some cases, one or both of pre-sample circuits 32, 34 may perform chopper-stabilized amplification to generate a chopper-stabilized amplified version of a respective input signal. For example, one or both of pre-sample circuits 32, 34 may include a chopper amplifier as described below with respect to FIG. 3.

In further examples, one or both of pre-sample circuits 32, 34 may convert a target frequency band of interest to a baseband in addition to amplifying the signal. For example, one or both of pre-sample circuits 32, 34 may include a frequency-converting chopper amplifier as described below with respect to FIG. 4. Converting a target frequency band of interest to baseband may correspond to causing a center frequency of the target frequency band to be substantially centered at a direct current (DC) frequency (e.g., zero Hertz (Hz)).

The sensing and analysis circuitry 30 in FIG. 2 may be versatile in the sense that each channel may be configured to be a power channel or a time domain channel. A power channel may use pre-sample circuits 32, 34 to amplify and convert a target frequency band of a respective input signal to baseband. The power channel may further use ADCs 16, 18 to sample the respective signal and generate a sampled signal of a particular target frequency band of the respective input signal. A time domain channel may use pre-sample circuits 32, 34 to amplify a respective input signal without performing any net frequency conversion, and ADCs 16, 18 to sample the respective signal to generate a wide-band sampled signal.

According to some aspects of this disclosure, one or more processing parameters for a particular channel may be adjusted to move spectral aggressors out of a target frequency band of interest in another channel. For example, one or more processing parameters for channel A may be configured to move spectral aggressors out of a target frequency band of interest in channel B. As another example, one or more processing parameters for channel B may be configured to move spectral aggressors out of a target frequency band of interest in channel A.

According to additional aspects of this disclosure, one or more processing parameters for a particular channel may be adjusted to move spectral aggressors out of a target frequency band of interest in that same particular channel. For example, one or more processing parameters for channel A may be configured to move spectral aggressors out of a target frequency band of interest in channel A. As another example, one or more processing parameters for channel B may be configured to move spectral aggressors out of a target frequency band of interest in channel B.

According to further aspects of this disclosure, one or more processing parameters for a particular type of channel may be adjusted to move spectral aggressors out of a target frequency band of another type of channel. For example, one or more processing parameters for a power domain channel may be configured to move spectral aggressors out of a target frequency band of interest in a time domain channel. As another example, one or more processing parameters for a time domain channel may be configured to move spectral aggressors out of a target frequency band of interest in a power domain channel.

According to additional aspects of this disclosure, one or more processing parameters for a particular type of channel may be adjusted to move spectral aggressors out of that same type of channel. For example, one or more processing parameters for a power domain channel may be configured to move spectral aggressors out of a target frequency band of interest in another power domain channel. As another example, one or more processing parameters for a time domain channel may be configured to move spectral aggressors out of a target frequency band of interest in another time domain channel.

An example of configuring the buffering rate of processor 20 and the sampling rate of one of ADCs 16, 18 to move spectral aggressors out of a target frequency band of interest will now be described with respect to an example sensing system. Prior to applying some aspects of this disclosure to the example sensing system, the sample rate for time-domain data was 200 Hz. 8 data points (per channel) were buffered by firmware executing on the processor (e.g., processor 20). The firmware then wrote the sampled data to an off-chip SRAM (e.g., memory 22). This resulted in a 25 Hz processing aggressor, which is right in the middle of the beta band (e.g., 15 to 35 Hz). The beta band may correspond to symptoms that are associated with epilepsy and Parkinson's disease.

In this case, to move the aggressor out of the beta band, the rate of buffering and SRAM writes was changed by modifying the firmware to perform processing after buffering 4 points of data rather than 8 points of data. This moved the aggressor to 50 Hz, which is outside of the beta band. In Europe, their line noise is at 50 Hz, so European systems may already perform notch-filtering at 50 Hz.

In another example, the sampling rate may be shifted higher, for example, to 422 Hz. By using the same buffering technique, this moves the aggressor to 105.5 Hz. In this case, information in the range of up to ~100 Hz can be analyzed without interference from the aggressor.

Figure 3:
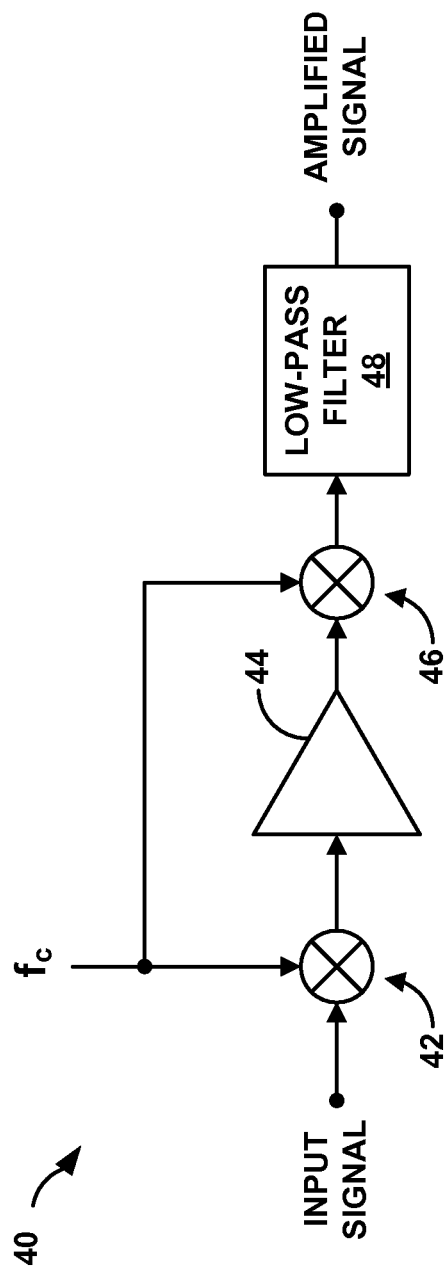
FIG. 3 is a block diagram illustrating an example chopper amplifier that may be used in the sensing and analysis circuitry of FIG. 2.

FIG. 3 is a block diagram illustrating an example chopper amplifier 40 that may be used in the sensing and analysis circuitry 30 of FIG. 2. For example, one or both of pre-sample circuits 32, 34 may, in some examples, include a chopper amplifier 40. Chopper amplifier 40 is configured to receive an input signal, and generate a chopper-stabilized amplified version of the input signal based on a chopper frequency (i.e., $f_c$). Chopper amplifier 40 includes a modulator 42, an amplifier 44, a demodulator 46, and a low-pass filter 48.

Modulator 42 modulates an amplitude of the input signal based on the chopper frequency (i.e., $f_c$) to produce a modulated signal. Amplifier 44 amplifies an amplitude of the modulated signal to produce an amplified signal. Demodulator 46 demodulates the amplified signal based on the chopper frequency (i.e., $f_c$) to produce a demodulated signal. Low-pass filter 48 low-pass filters the demodulated signal to generate a chopper-stabilized amplified version of the input signal.

Modulating and demodulating a signal based on a chopper frequency may refer, respectively, to modulating and demodulating the signal at the chopper frequency. In other words, modulator 42 and demodulator 46 may multiply a signal received by the respective modulator or demodulator with the chopper frequency to produce an output signal (e.g., a modulated signal or a demodulated signal). In some examples, demodulator 46 may also be referred to as a modulator. In some cases, modulator 42 and demodulator 46 may be constructed from one or more switches that are switched at the chopper frequency.

Amplifier 44 may be any type of amplifier with any combination of single-ended or differential inputs and outputs. If the inputs to amplifier 44 are single-ended, then amplifier 44 may amplify the single-ended input signal to generate an amplified version of the input signal. On the other hand, if the inputs to amplifier 44 are differential, then amplifier 44 may amplify a difference between the input signals to generate an amplified version of the input signal. Low-pass filter 48 may be any type of low-pass filter including, e.g., an integrator or a type of low-pass filter that includes a pass band and a stop band.

Figure 6:
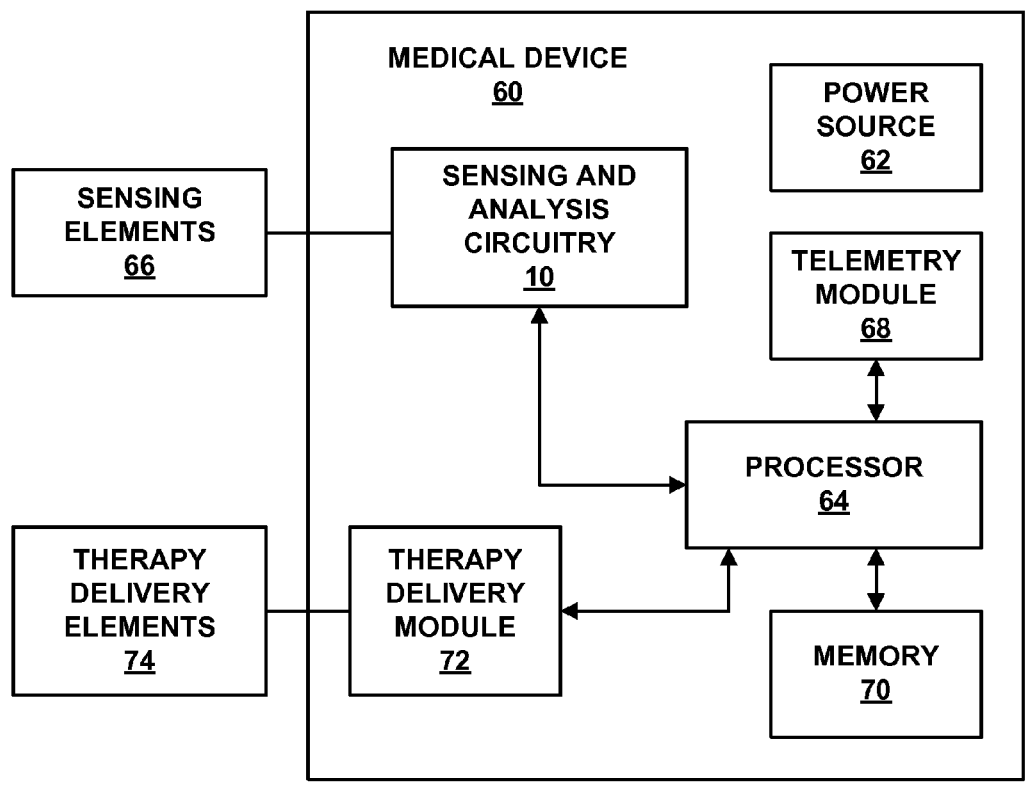
FIG. 6 is block diagram illustrating an example medical device in which the spectral aggressor control techniques of this disclosure may be implemented.

Although amplifier 44 and demodulator 46 are illustrated in FIG. 3 as being separate components, in some examples, amplifier 44 and demodulator 46 may be integrated into a single mixer amplifier component. The single mixer amplifier component may be a modified folded-cascode amplifier with switching at low impedance nodes. An example of a modified folded-cascode amplifier with switching at low impedance nodes is shown in FIG. 6 of and described in the corresponding description of U.S. Pat. No. 7,385,443, issued Jun. 10, 2008, to Timothy J. Denison, entitled "Chopper Stabilized Instrumentation Amplifier," the entire content of which is incorporated herein by reference. Other examples of modified folded-cascode amplifiers with switching at low impedance nodes are shown in FIGS. 3A and 3B of and described in the corresponding description of U.S. Pat. No. 7,714,757, issued May 11, 2010, to Timothy J. Denison et al., entitled "Chopper-stabilized analog-to-digital converter," the entire content of which is incorporated herein by reference. An additional example of a modified folded-cascode amplifier with switching at low impedance nodes is shown in FIG. 12 of and described in the corresponding description of U.S. Patent Publication No. 2009/0082691, published Mar. 26, 2009, to Timothy J. Denison et al., entitled "FREQUENCY SELECTIVE MONITORING OF PHYSIOLOGICAL SIGNALS," the entire content of which is incorporated herein by reference.

The chopper amplifier illustrated in FIG. 3 is merely one example of a chopper amplifier that may be used in accordance with the techniques of this disclosure. In further examples, chopper amplifier 40 may be a nested chopper amplifier, may include in-phase and quadrature phase signal processing pathways, or may be a nested chopper amplifier that includes in-phase and quadrature phase signal processing pathways. An example of a nested chopper amplifier that includes in-phase and quadrature phase signal processing pathways is shown in FIG. 26 of U.S. Patent Publication No. 2009/0082691, published Mar. 26, 2009, to Timothy J. Denison et al., entitled "FREQUENCY SELECTIVE MONITORING OF PHYSIOLOGICAL SIGNALS," the entire content of which is incorporated herein by reference. The nested chopper amplifier in FIG. 26 may, in some examples, have a delta set equal to zero.

Figure 4:
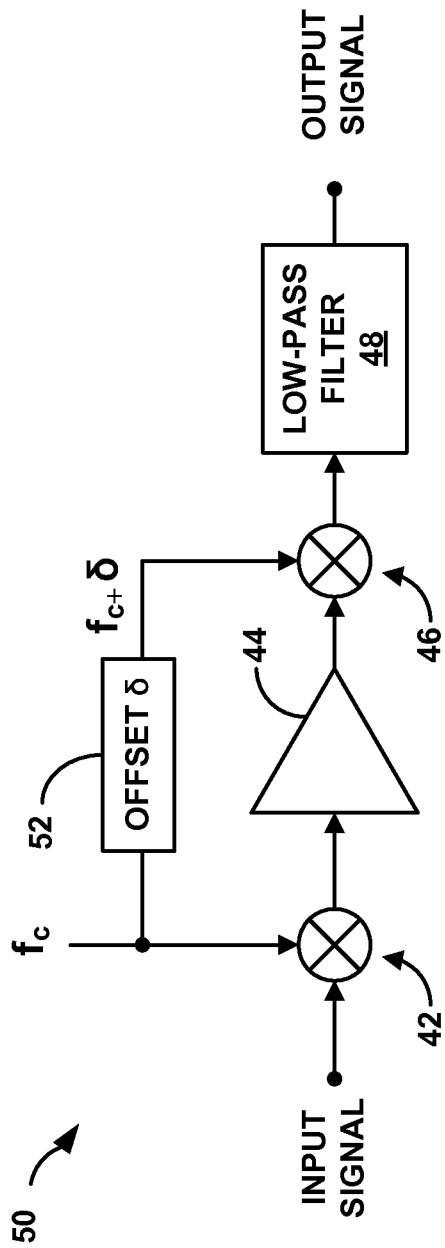
FIG. 4 is a block diagram illustrating an example chopper-stabilized amplifier that performs frequency conversion and that may be used in the sensing and analysis circuitry of FIG. 2.

FIG. 4 is a block diagram illustrating an example chopper-stabilized amplifier 50 that performs frequency conversion and that may be used in the sensing and analysis circuitry 30 of FIG. 2. For example, one or both of pre-sample circuits 32, 34 may, in some examples, include a chopper-stabilized amplifier 50. The chopper-stabilized amplifier 50 shown in FIG. 4 may be configured to perform net frequency conversion in addition to amplification. In other words, chopper amplifier 50 may convert a target frequency band of interest to a baseband in addition to amplifying the signal. Converting a target frequency band of interest to baseband may correspond to causing a center frequency of the target frequency band to be substantially centered at a direct current (DC) frequency (e.g., zero Hertz (Hz)).

Chopper amplifier 50 includes components that are substantially similar to those already discussed above with respect to chopper amplifier 40 in FIG. 3 except that chopper amplifier 50 also includes a frequency shifter 52 that is configured to offset the chopper frequency (i.e., $f_c$) by an offset (i.e., $\delta$) to generate a demodulator frequency (i.e., $f_{c+\delta}$). In chopper amplifier 50, modulator 42 modulates an amplitude of the input signal based on a first chopper frequency (i.e., $f_c$) to produce a modulated signal. Amplifier 44 amplifies an amplitude of the modulated signal to produce an amplified signal. Demodulator 46 demodulates the amplified signal based on a second chopper frequency (i.e., $f_{c+\delta}$) to produce a demodulated signal. Low-pass filter 48 low-pass filters the demodulated signal to generate a chopper-stabilized amplified version of the input signal. The offset between the chopper frequencies causes chopper amplifier 50 to perform a net frequency conversion.

Although amplifier 44 and demodulator 46 are illustrated in FIG. 4 as being separate components, in some examples, amplifier 44 and demodulator 46 may be integrated into a single mixer amplifier component. The single mixer amplifier component may be a modified folded-cascode amplifier with switching at low impedance nodes. An example of a modified folded-cascode amplifier with switching at low impedance nodes is shown in FIG. 6 of and described in the corresponding description of U.S. Pat. No. 7,385,443, issued Jun. 10, 2008, to Timothy J. Denison, entitled "Chopper Stabilized Instrumentation Amplifier," the entire content of which is incorporated herein by reference. Other examples of modified folded-cascode amplifiers with switching at low impedance nodes are shown in FIGS. 3A and 3B of and described in the corresponding description of U.S. Pat. No. 7,714,757, issued May 11, 2010, to Timothy J. Denison et al., entitled "Chopper-stabilized analog-to-digital converter," the entire content of which is incorporated herein by reference. An additional example of a modified folded-cascode amplifier with switching at low impedance nodes is shown in FIG. 12 of and described in the corresponding description of U.S. Patent Publication No. 2009/0082691, published Mar. 26, 2009, to Timothy J. Denison et al., entitled "FREQUENCY SELECTIVE MONITORING OF PHYSIOLOGICAL SIGNALS," the entire content of which is incorporated herein by reference.

The chopper amplifier illustrated in FIG. 4 is merely one example of a chopper amplifier that may be used in accordance with the techniques of this disclosure. In further examples, chopper amplifier 40 may be a nested chopper amplifier, may include in-phase and quadrature phase signal processing pathways, or may be a nested chopper amplifier that includes in-phase and quadrature phase signal processing pathways. An example of a nested chopper amplifier that includes in-phase and quadrature phase signal processing pathways is shown in FIG. 26 of U.S. Patent Publication No. 2009/0082691, published Mar. 26, 2009, to Timothy J. Denison et al., entitled "FREQUENCY SELECTIVE MONITORING OF PHYSIOLOGICAL SIGNALS," the entire content of which is incorporated herein by reference.

FIGS. 5A and 5B are conceptual diagrams illustrating an example of how the algorithm subdivision techniques described in this disclosure may be used to move spectral aggressors out of a target frequency band of interest. When a processor is causing aggressors by entering and exiting sleep mode to perform processing as described above, in some examples, processor 20 may chop up the processing (i.e., subdivide the processing of an algorithm into separate execution units that are processed during different time intervals), thereby changing the frequency of the aggressor.

An example of using algorithm subdivision to control spectral aggressors will now be described. Consider example sensing and analysis circuitry 30 (FIG. 2) that is configured to sample time-domain data at 200 Hz and power channel data at 5 Hz. FIG. 5A depicts this example where processor 20 is processing an algorithm at a 5 Hz algorithm processing rate with no subdivision of the algorithm (e.g., an algorithm subdivision factor of one). If an algorithm runs at the 5 Hz rate, it could impart a 5 Hz aggressor upon the time-domain data that is collected. Note that the harmonics of an aggressor may also get included in spectral analysis. In this case, an aggressor may appear every 5 Hz.

According to some aspects of this disclosure, processor 20 may split up the processing and distribute the processing throughout the algorithm processing time interval, which may move the aggressor to a higher frequency. FIG. 5B depicts an example where the processing for the algorithm has been split up into 8 separate pieces (e.g., an algorithm subdivision factor of eight). This moves the aggressor from 5 Hz (FIG. 5A) to 40 Hz (FIG. 5B). The algorithm subdivision techniques of this disclosure may be used, in some examples, to move the aggressor upward in frequency.

FIG. 6 is block diagram illustrating an example medical device 60 in which the spectral aggressor control techniques of this disclosure may be implemented. Sensing and analysis circuitry 10 may monitor and/or analyze physiological signals associated with a patient in selected frequency bands. The physiological signals may be relatively low frequency signals, and may have frequency bands of interest in a range of approximately 1 to 1000 Hertz (Hz) and, more particularly, in a range of approximately 1 to 500 Hz. For example, 1 Hz oscillations may be relevant for sleep state analysis, while fast ripples in a range of approximately 200 to 500 Hz or higher may be relevant for analysis of epilepsy. In general, frequencies in the selected frequency band are less than or equal to approximately 1000 Hz, more particularly less than or equal to approximately 500 Hz, and still more particularly less than or equal to approximately 100 Hz. For EEG signals, as an example, selected frequency bands may fall in the ranges of approximately 5 to 15 Hz (alpha band), 15 to 35 Hz (beta band), and 30 to 80 Hz (gamma band). Characteristics of the signal in selected frequency bands may be useful in controlling therapy, such as electrical stimulation or drug delivery, either by initiation of delivery of therapy or adjustment of therapy parameters. Adjustment of therapy parameters may include adjustment of pulse amplitude, pulse rate, pulse width, electrode combination or the like for electrical stimulation, or adjustment of dosage, rate, frequency, lockout interval, or the like for drug delivery.

As illustrated in FIG. 6, medical device 60 may also include a power source 62, such as a rechargeable or nonrechargeable battery, a processor 64, a telemetry module 68, a memory 70, and a therapy delivery module 72. In addition, in the example of FIG. 6, sensing and analysis circuitry 10 is connected to sensing elements 66 that are positioned at a desired location relative to the patient and that detect the physiological signal. Sensing elements 66 may include a set of electrodes for sensing electrical signals. The electrodes may be, for example, implantable electrodes deployed on a lead or external surface electrodes. Sensing elements 66 may be deployed at selected tissue sites or on selected surfaces of a human patient, such as within the brain, proximate the spinal cord, on the scalp, or elsewhere. As an example, scalp electrodes may be used to measure or record EEG signals. As another example, electrodes implanted at the surface of the cortex may be used to measure or record ECoG signals. Therapy delivery module 72 may be connected to therapy delivery elements 74, such as one or more electrodes deployed on a lead or drug delivery conduits, which may be positioned at a desired location relative to the patient to deliver therapy to the patient in response to the monitored physiological signal.

In some embodiments, medical device 60 may comprise an implantable medical device capable of being implanted within the patient. In this case, sensing elements 66 may be positioned at a desired location within the patient to detect the physiological signal. Further, therapy delivery elements 74 may be positioned at a desired location within the patient to deliver the therapy, such as electrical stimulation, drug delivery or internal audio or visual cueing. In other embodiments, medical device 60 may comprise an external medical device with sensing elements positioned at a desired location adjacent the patient to detect the physiological signal. In addition, therapy delivery elements 74 may be positioned at a desired location external to the patient to deliver the therapy, such as external audio, visual or tactile cueing via lights, displays, speakers, or the like.

Processor 64, sensing and analysis circuitry 10, telemetry module 68, memory 70, and therapy delivery module 72 may receive operating power from power source 62. Power source 62 may take the form of a small, rechargeable or non-rechargeable battery, or an inductive power interface that receives inductively coupled energy. In the case of a rechargeable battery, power source 62 similarly may include an inductive power interface for transfer of recharge power.

Processor 64 may include one or more microprocessors, microcontrollers, digital signal processors (DSPs), application specific integrated circuits (ASICs), field programmable gate array (FPGAs), discrete logic circuitry, or a combination of such components. In some examples, processor 64 in medical device 60 may be the same processor as processor 20 in sensing and analysis circuitry 10. In additional examples, processor in medical device 60 may be different than processor 20 in sensing and analysis circuitry 10.

Memory 70 may store therapy instructions that are available to be selected by processor 64 in response to receiving a patient therapy trigger from sensing and analysis circuitry 10. In addition, processor 64 may be configured to record diagnostic information, such as sensed signals, signal characteristics, or the like in memory 70 or another memory or storage device. Memory 70 may include any combination of volatile, non-volatile, removable, magnetic, optical, or solid state media, such as read-only memory (ROM), random access memory (RAM), electronically-erasable programmable ROM (EEPROM), flash memory, or the like.

Sensing and analysis circuitry 10 may monitor a variety of signals via a variety of different sensing elements 66, such as a pressure sensing element, an accelerometer, an activity monitor, an impedance monitor, an electrical signal monitor or other monitor configured to monitor heart sounds, brain signals, and/or other physiological signals. As an illustration, sensing elements 66 may comprise one or more electrodes located on a lead implanted at a target site within the patient and electrically coupled to sensing and analysis circuitry 10 via conductors. Sensing and analysis circuitry 10 may monitor the signals obtained from sensing elements 66. Sensing and analysis circuitry 10 may include suitable electrical interconnections to sensing elements 66 and other components, as necessary.

A lead may carry one electrode or multiple electrodes, such as ring electrodes, segmented electrodes or electrodes arranged in a planar or non-planar array, e.g., on a paddle lead. Medical device 60 may be implantable or external. Such leads may carry sense electrodes or a combination of sense and stimulation electrodes. In some cases, different leads may be dedicated to sensing and stimulation functions. If external, medical device 60 may be coupled to one or more leads carrying sense and/or stimulation electrodes via a percutaneous extension. As a further illustration, sensing elements 66 may be surface electrodes suitable for placement on scalp, face, chest, or elsewhere on a patient, in which case such electrodes may be coupled to sensing and analysis circuitry 10 via conductors within external leads. Sensing elements 66 may further comprise combinations of electrodes provided on one or more implantable leads and on or within a housing of medical device 60, or other electrode arrangements.

In general, sensing elements 66 provide a measurement of a physiological signal associated with the patient by translating the signal to an output voltage or current. Sensing and analysis circuitry 10 may receive the measured physiological signal as an input signal, pre-process the physiological signal to produce a processed signal, sample the processed signal at a sampling rate to generate a sampled signal, and process the sampled signal. In some examples, processing the sampled signal may include performing one or more processing algorithms with respect to the sampled signal. The one or more processing algorithms may measure one or more characteristics of a target frequency band of the sampled signal and/or may store the sampled signal into a memory (e.g., memory 70).

In some examples, sensing and analysis circuitry 10 may measure the power in the target frequency band or power fluctuations in the target frequency band. The measured power may be used to determine whether the delivery of therapy is triggered or initiated and/or whether the recording of diagnostic information is triggered or initiated.

In some examples, sensing and analysis circuitry 10 may generate a signal indicative of the power of a target frequency band of the physiological signal and/or a signal indicative of power fluctuation of a target frequency band of the physiological signal. In such examples, processor 64 may trigger the delivery of therapy and/or trigger the recording of diagnostic information based on the signal indicative of the power of the target frequency band and/or the signal indicative of power fluctuation of the target frequency band.

In further examples, sensing and analysis circuitry 10 may output a trigger signal to processor 64 to control therapy and/or record diagnostic information. In such examples, processor 64 may receive the trigger signal and initiate delivery of therapy or adjust one or more therapy parameters specified in memory 70.

Processor 64 may output therapy instructions to therapy delivery module 72 to initiate or adjust delivery of therapy. Therapy delivery module 72 may include a stimulation generator that delivers stimulation therapy to the patient via therapy delivery elements 74 in response to receiving the therapy instructions. Therapy delivery elements 74 may be electrodes carried on one or more leads, electrodes on the housing of medical device 60, or electrodes on both a lead and the medical device housing. Alternatively, therapy delivery module 72 may include a fluid delivery device, such as a drug delivery device, including a fluid reservoir and one or more fluid delivery conduits. For cueing applications, therapy delivery module 72 may include one or more speakers, one or more lights, one or more display screens, or any combination thereof.

In some cases, as described above, therapy delivery module 72 may include a stimulation generator or other stimulation circuitry that delivers electrical signals, e.g., pulses or substantially continuous signals, such as sinusoidal signals, to the patient via at least some of the electrodes that form therapy delivery elements 74 under the control of the therapy instructions received from processor 64. Processor 64 may control therapy delivery module 72 to deliver electrical stimulation with pulse voltage or current amplitudes, pulse widths, and frequencies (i.e., pulse rates), and electrode combinations specified by the programs of the selected therapy instructions, e.g., as stored in memory 70. Processor 64 may also control therapy delivery module 72 to deliver each pulse, or a burst of pulses, according to a different program of the therapy instructions, such that multiple programs of stimulation are delivered an interleaved or alternating basis. In some embodiments, processor 64 may control therapy delivery module 72 to deliver a substantially continuous stimulation waveform rather than pulsed stimulation.

In other cases, as described above, therapy delivery module 72 may include a one or more fluid reservoirs and one or more pump units that pump fluid from the fluid reservoirs to the target site through the fluid delivery devices that form therapy delivery elements 74 under the control of the therapy instructions received from processor 64. For example, processor 64 may control which drugs are delivered and the dosage, rate and lockout interval of the drugs delivered. The fluid reservoirs may contain a drug or mixture of drugs. The fluid reservoirs may provide access for filling, e.g., by percutaneous injection of fluid via a self-sealing injection port. The fluid delivery devices may comprise, for example, fluid delivery conduits in the form of catheters that deliver, i.e., infuse or disperse, drugs from the fluid reservoirs to the same or different target sites.

In some cases, therapy delivery module 72 may include an audio signal generator, a visual signal, or a tactile stimulus (e.g., vibration) generator for cueing to disrupt akinesia or treat other conditions. Processor 64 may control therapy delivery module 72 to deliver audio, visual or tactile cueing with different parameters, such as amplitude, frequency, or the like, as specified by programs stored in memory 26.

Processor 64 also may control a telemetry module 68 to exchange information with an external programmer, such as a clinician programmer and/or patient programmer, by wireless, radio frequency (RF) telemetry. Processor 64 may control telemetry module 68 to communicate with the external programmer on a continuous basis, at periodic intervals, or upon request from the programmer. The programmer may, in turn, be connected to a computer that can program the device for algorithm and sensing adjustments, for issuing commands, for uplinking recorded loop data and for providing analysis. In addition, in some embodiments, telemetry module 68 may support wireless communication with one or more wireless sensors or sensing elements that sense physiological signals and transmit the signals to sensing and analysis circuitry 10 by wireless transmission.

Figure 7:
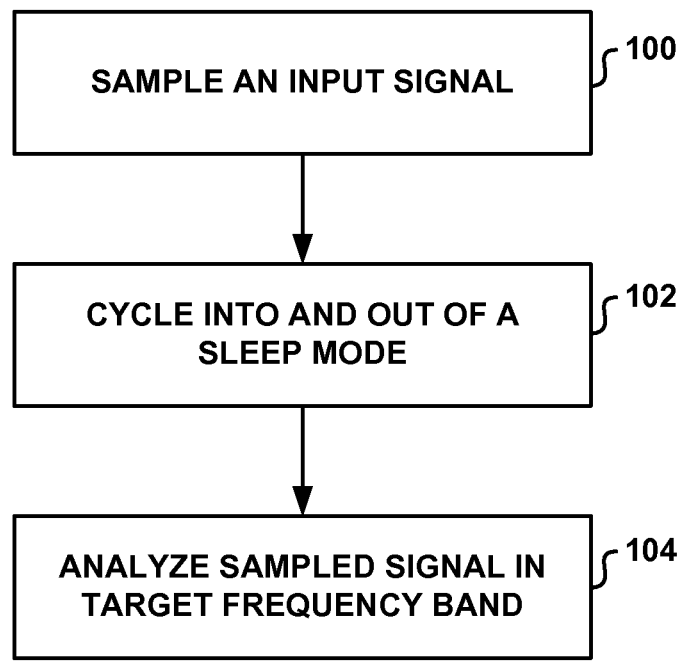
FIG. 7 is a flow diagram illustrating an example technique for controlling spectral aggressors according to this disclosure.

FIG. 7 is a flow diagram illustrating an example technique for controlling spectral aggressors according to this disclosure. ADCs 16, 18 sample an input signal (100). Processor 20 cycles into and out of a sleep mode (102). For example, processor 20 may cycle between an algorithm processing mode and a sleep mode based on a sleep cycle rate. Processor 20 analyzes information contained in a target frequency band of the sampled signal (106). For example, processor 20 may determine a power magnitude or an amount or frequency of power fluctuation. In some examples, in addition to or in lieu of analyzing the information contained in the target frequency band, processor 20 may store the sampled data in memory 22

Pre-sample circuits 32, 34 and processor 20 may both be electrically coupled to a power distribution network 14 that is electrically coupled to a common power source 12. The sleep cycle rate may cause spectral interference to propagate through power distribution network 14 and into the sampled signal via ADCs 16, 18.

According to this disclosure, the sleep cycle rate may further cause the spectral interference that is generated due to the sleep cycle rate to occur in one or both of the sampled signals produced by ADCs 16, 18 at one or more frequencies that are outside of the target frequency band of the sampled signals. For example, one or more of the algorithm processing rate for processor 20, the buffering rate for processor 20, the sampling rate for ADCs 16, 18, the execution unit processing rate for processor 20, and the algorithm subdivision factor for processor 20 may be configured such that the spectral interference caused by the sleep cycle rate occurs in one or both of the sampled signals produced by ADCs 16, 18 at one or more frequencies that are outside of one or more target frequency bands of the sampled signals. Moving spectral aggressors that are caused by the sleep mode cycling of processor 20 to portions of the sampled signal that are outside of the target frequency band of interest may reduce the amount of noise in the target frequency band of the sampled signal, thereby improving the ability of sensing and analysis circuitry 30 to analyze one or more characteristics of a target frequency band of one or both of the sampled signals produced by ADCs 16, 18.

The techniques of this disclosure may be used, in some examples, to reduce noise caused by aggressors in a brain signal sensing system and/or to perform rate control of aggressors for spectral processing. In some examples, the techniques of this disclosure may be implemented in an implantable neurostimulator that performs deep brain stimulation (DBS).

Sensing of local field potentials (LFPs) in the brain of patients may be performed in an implantable medical device that includes frequency conversion chopper amplifiers similar to those depicted in FIG. 4. The information content of LFPs may be contained within its spectral characteristics. When a noise source (an aggressor) occurs at a rate that is in the frequency band of interest, it can ruin and/or degrade the information content of the sensed signal. The techniques of this disclosure may, in some examples, deal with these aggressors to improve sensing capability.

In some examples, noise may refer to the mixing of anything other than the signal of interest with the signal of interest. Some types of noise sources, such as, e.g., line noise and thermal noise may contaminate a signal. In some cases, a noise source may come from within the sensing device itself. These aggressors may be related to digital signals toggling and interfering with the analog sensing circuitry. In some examples, shielding and ground planes may be used to deal with this kind of aggressor.

In some examples, the techniques of this disclosure may deal with aggressors that are internal to a sensing system and that are the under the control of the system designers. The techniques of this disclosure may, in some examples, be used to change the nature of in-system aggressors to reduce their effects on the signals acquired.

In some examples, a processor may sample data, store sampled data, and execute algorithms with respect to the sampled data. In some cases the processor may have a low-current sleep mode that can be used whenever there is no active processing in order to limit the current drain of the processor. In general, keeping the duty cycle of the processing/sleep cycle as low as possible may limit the current draw.

One problem with a relatively low duty cycle is that the processor may have fluctuations in the instantaneous current draw when it cycles between awake and sleep states. For example, the duty cycling of the sense processor may cause fluctuation in the supply voltage to the ADCs, which may result in an aggressor that acts at a rate equal to that of the duty cycling.

One solution to deal with this aggressor is to completely eliminate the aggressor. Sometimes this may be very inconvenient or not possible. For example, it may be possible to reduce the processing aggressor from occurring by adding a regulator. However, a regulator may not completely eliminate the aggressor and may require some additional current draw of its own. This disclosure describes techniques to move the aggressor out of the frequency band of interest without requiring an additional regulator to be added to a sensing system in order to remove the aggressor.

In some examples, the techniques of this disclosure may change the rate of algorithm processing (e.g., the algorithm processing rate) in order to move in-system aggressors away from areas of interest. In further examples, the techniques of this disclosure may chop up and schedule processing at rates outside of the target frequency band in order to move in-system aggressors away from areas of interest. In additional examples, the techniques of this disclosure may change the sample rate in order to move in-system aggressors away from areas of interest.

Various techniques described in this disclosure may be implemented in hardware, software, firmware or any combination thereof. For example, various aspects of the techniques may be implemented within or in conjunction with one or more microprocessors, digital signal processors (DSPs), application specific integrated circuits (ASICs), field programmable logic arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry.

When implemented in software, the functionality ascribed to the systems and devices described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic media, optical media, or the like. The instructions may be executed to cause a processor to perform or support one or more aspects of the functionality described in this disclosure.

Various aspects and examples have been described. However, modifications can be made to the structure or techniques of this disclosure without departing from the scope of the following claims.

The invention claimed is:

1. A signal monitoring device comprising:
a power source;
a power distribution network electrically coupled to the power source;
an analog-to-digital converter electrically coupled to the power distribution network and configured to sample an input signal to produce a sampled signal; and
a processor electrically coupled to the power distribution network and configured to cycle between an algorithm processing mode and a sleep mode based on a sleep cycle rate,
wherein the sleep cycle rate causes spectral interference to propagate through the power distribution network and into the sampled signal via the analog-to-digital converter, and
wherein the sleep cycle rate further causes the spectral interference that is generated due to the sleep cycle rate to occur in the sampled signal at one or more frequencies that are outside of a target frequency band of the sampled signal.

2. The device of claim 1, wherein the sleep cycle rate is configured such that the spectral interference caused by the sleep cycle rate occurs in the sampled signal at the one or more frequencies that are outside of the target frequency band of the sampled signal.

3. The device of claim 2, wherein the sleep cycle rate is configured such that the sleep cycle rate is greater than an upper bound frequency of the target frequency band of the sampled signal.

4. The device of claim 2, wherein the sleep cycle rate is configured such that the sleep cycle rate is less than a lower bound frequency of the target frequency band of the sampled signal.

5. The device of claim 1,
wherein the processor is further configured to invoke instances of a processing algorithm at an algorithm processing rate to process the sampled signal,
wherein the sleep cycle rate is configured to be equal to the algorithm processing rate, and
wherein the algorithm processing rate is configured such that the spectral interference caused by the sleep cycle rate occurs in the sampled signal at the one or more frequencies that are outside of the target frequency band of the sampled signal.

6. The device of claim 5, wherein the algorithm processing rate is configured such that the sleep cycle rate is greater than an upper bound frequency of the target frequency band of the sampled signal or less than a lower bound frequency of the target frequency band of the sampled signal.

7. The device of claim 1,
wherein the analog-to-digital converter is a first analog-to-digital converter, wherein the input signal is a first input signal, wherein the sampled signal is a first sampled signal,
wherein the device further comprises a second analog-to-digital converter configured to sample a second input signal to produce a second sampled signal,
wherein the processor is further configured to invoke instances of a processing algorithm at an algorithm processing rate to process the second sampled signal,
wherein the sleep cycle rate is configured to be equal to the algorithm processing rate, and
wherein the algorithm processing rate is configured such that the spectral interference caused by the sleep cycle rate occurs in the first sampled signal at the one or more frequencies that are outside of the target frequency band of the first sampled signal.

8. The device of claim 7, wherein the algorithm processing rate is configured such that the sleep cycle rate is greater than an upper bound frequency of the target frequency band of the first sampled signal or less than a lower bound frequency of the target frequency band of the first sampled signal.

9. The device of claim 1,
wherein the analog-to-digital converter is further configured to sample the input signal at a sampling rate,
wherein the processor is further configured to buffer the sampled signal at a buffering rate, the buffering rate being indicative of a number of data samples to buffer per invocation of a processing algorithm,
wherein the processor is further configured to invoke instances of the processing algorithm at a rate equal to a quotient of the sampling rate divided by the buffering rate to process the sampled signal,
wherein the sleep cycle rate is configured to be equal to the quotient of the sampling rate divided by the buffering rate, and
wherein the buffering rate and the sampling rate are configured such that the spectral interference caused by the sleep cycle rate occurs in the sampled signal at the one or more frequencies that are outside of the target frequency band of the sampled signal.

10. The device of claim 9, wherein the buffering rate and the sampling rate are configured such that the sleep cycle rate is greater than an upper bound frequency of the target frequency band of the sampled signal or less than a lower bound frequency of the target frequency band of the sampled signal.

11. The device of claim 1,
wherein the analog-to-digital converter is a first analog-to-digital converter, wherein the input signal is a first input signal, wherein the sampled signal is a first sampled signal,
wherein the device further comprises a second analog-to-digital converter configured to sample a second input signal at a sampling rate to produce a second sampled signal,
wherein the processor is further configured to buffer the second sampled signal at a buffering rate, the buffering rate being indicative of a number of data samples to buffer per invocation of a processing algorithm,
wherein the processor is further configured to invoke instances of the processing algorithm at a rate equal to a quotient of the sampling rate divided by the buffering rate to process the second sampled signal,
wherein the sleep cycle rate is configured to be equal to the quotient of the sampling rate divided by the buffering rate, and
wherein the buffering rate and the sampling rate are configured such that the spectral interference caused by the sleep cycle rate occurs in the first sampled signal at the one or more frequencies that are outside of the target frequency band of the first sampled signal.

12. The device of claim 11, wherein the buffering rate and the sampling rate are configured such that the sleep cycle rate is greater than an upper bound frequency of the target frequency band of the first sampled signal or less than a lower bound frequency of the target frequency band of the first sampled signal.

13. The device of claim 1,
wherein the processor is further configured to invoke instances of a processing algorithm at an algorithm processing rate to process the sampled signal,
wherein the processor is further configured to, for each of the instances of the processing algorithm that are invoked, execute the respective instance of the processing algorithm during a number of separate time intervals, each of the separate time intervals being separated from adjacent time intervals by a time interval where the respective processing algorithm is not executed, the number of separate time intervals being determined by an algorithm subdivision factor,
wherein the sleep cycle rate is configured to be equal to a product of an algorithm processing rate and the algorithm subdivision factor, and
wherein the algorithm processing rate and the algorithm subdivision factor are configured such that the spectral interference caused by the sleep cycle rate occurs in the sampled signal at the one or more frequencies that are outside of the target frequency band of the sampled signal.

14. The device of claim 13, wherein the algorithm processing rate and the algorithm subdivision factor are configured such that the sleep cycle rate is greater than an upper bound frequency of the target frequency band of the sampled signal or less than a lower bound frequency of the target frequency band of the sampled signal.

15. The device of claim 13,
wherein the analog-to-digital converter is further configured to sample the input signal at a sampling rate to produce the sampled signal,
wherein the processor is further configured to buffer the sampled signal at a buffering rate, the buffering rate being indicative of a number of data samples to buffer per invocation of the processing algorithm,
wherein the algorithm processing rate is equal to a quotient of the sampling rate divided by the buffering rate, and
wherein the sampling rate, the buffering rate and the algorithm subdivision factor are configured such that the spectral interference caused by the sleep cycle rate occurs in the sampled signal at the one or more frequencies that are outside of the target frequency band of the sampled signal.

16. The device of claim 1,
wherein the analog-to-digital converter is a first analog-to-digital converter, wherein the input signal is a first input signal, wherein the sampled signal is a first sampled signal,
wherein the device further comprises a second analog-to-digital converter configured to sample a second input signal to produce a second sampled signal,
wherein the processor is further configured to invoke instances of a processing algorithm at an algorithm processing rate to process the second sampled signal,
wherein the processor is further configured to, for each of the instances of the processing algorithm that are invoked, execute the respective instance of the processing algorithm during a number of separate time intervals, each of the separate time intervals being separated from adjacent time intervals by a time interval where the respective processing algorithm is not executed, the number of separate time intervals being determined by an algorithm subdivision factor,
wherein the sleep cycle rate is configured to be equal to a product of the algorithm processing rate and the algorithm subdivision factor, and
wherein the algorithm processing rate and the algorithm subdivision factor are configured such that the spectral interference caused by the sleep cycle rate occurs in the first sampled signal at the one or more frequencies that are outside of the target frequency band of the first sampled signal.

17. The device of claim 16, wherein the algorithm processing rate and the algorithm subdivision factor are configured such that the sleep cycle rate is greater than an upper bound frequency of the target frequency band of the first sampled signal or less than a lower bound frequency of the target frequency band of the first sampled signal.

18. The device of claim 16,
wherein the second analog-to-digital converter is further configured to sample the second input signal at a sampling rate to produce the second sampled signal,
wherein the processor is further configured to buffer the second sampled signal at a buffering rate, the buffering rate being indicative of a number of data samples to buffer per invocation of the processing algorithm,
wherein the algorithm processing rate is equal to a quotient of the sampling rate divided by the buffering rate, and
wherein the sampling rate, the buffering rate and the algorithm subdivision factor are configured such that the spectral interference caused by the sleep cycle rate occurs in the first sampled signal at the one or more frequencies that are outside of the target frequency band of the first sampled signal.

19. The device of claim 1, wherein the physiological signal is brain signal and the target frequency band is one of an alpha, beta, gamma or fast ripple frequency band of the brain signal.

20. The device of claim 19, wherein the brain signal comprises at least one of an electroencephalogram (EEG) signal, an electrocorticogram (ECoG) signal, a local field potential (LFP) signal, or a single cell action potential signal.

21. The device of claim 1, wherein the processor is further configured to determine at least one of a power level of the target frequency band in the sampled signal and a power fluctuation of the target frequency band in the sampled signal.

22. The device of claim 1, wherein the processor is further configured to analyze the target frequency band of the sampled signal.

23. The device of claim 1, wherein the target frequency band of the sampled signal is a target frequency band to be analyzed during post-processing of the sampled signal.

24. The device of claim 1, wherein the power source, the power distribution network, the analog-to-digital converter, and the processor are included in an implantable medical device.

25. A method for monitoring signals comprising:
sampling, with an analog-to-digital converter, an input signal to produce a sampled signal; and
cycling a processor between an algorithm processing mode and a sleep mode based on a sleep cycle rate,
wherein the analog-to-digital converter and the processor are both electrically coupled to a power distribution network that is electrically coupled to a power source,
wherein the sleep cycle rate causes spectral interference to propagate through the power distribution network and into the sampled signal via the analog-to-digital converter, and
wherein the sleep cycle rate further causes the spectral interference that is generated due to the sleep cycle rate to occur in the sampled signal at one or more frequencies that are outside of a target frequency band of the sampled signal.

26. The method of claim 25, wherein the sleep cycle rate is configured such that the spectral interference caused by the sleep cycle rate occurs in the sampled signal at the one or more frequencies that are outside of the target frequency band of the sampled signal.

27. The method of claim 26, wherein the sleep cycle rate is configured such that the sleep cycle rate is greater than an upper bound frequency of the target frequency band of the sampled signal.

28. The method of claim 26, wherein the sleep cycle rate is configured such that the sleep cycle rate is less than a lower bound frequency of the target frequency band of the sampled signal.

29. The method of claim 25, further comprising:
invoking, with the processor, instances of a processing algorithm at an algorithm processing rate to process the sampled signal,
wherein the sleep cycle rate is configured to be equal to the algorithm processing rate, and
wherein the algorithm processing rate is configured such that the spectral interference caused by the sleep cycle rate occurs in the sampled signal at the one or more frequencies that are outside of the target frequency band of the sampled signal.

30. The method of claim 29, wherein the algorithm processing rate is configured such that the sleep cycle rate is greater than an upper bound frequency of the target frequency band of the sampled signal or less than a lower bound frequency of the target frequency band of the sampled signal.

31. The method of claim 25,
wherein the analog-to-digital converter is a first analog-to-digital converter, wherein the input signal is a first input signal, wherein the sampled signal is a first sampled signal,
wherein the method further comprises:
sampling, with a second analog-to-digital converter, a second input signal to produce a second sampled signal,
invoking, with the processor, instances of a processing algorithm at an algorithm processing rate to process the second sampled signal,
wherein the sleep cycle rate is configured to be equal to the algorithm processing rate, and
wherein the algorithm processing rate is configured such that the spectral interference caused by the sleep cycle rate occurs in the first sampled signal at the one or more frequencies that are outside of the target frequency band of the first sampled signal.

32. The method of claim 31, wherein the algorithm processing rate is configured such that the sleep cycle rate is greater than an upper bound frequency of the target frequency band of the first sampled signal or less than a lower bound frequency of the target frequency band of the first sampled signal.

33. The method of claim 25, further comprising:
sampling, with the analog-to-digital converter, the input signal at a sampling rate;
buffering, with the processor, the sampled signal at a buffering rate, the buffering rate being indicative of a number of data samples to buffer per invocation of a processing algorithm;
invoking, with the processor, instances of the processing algorithm at a rate equal to a quotient of the sampling rate divided by the buffering rate to process the sampled signal,
wherein the sleep cycle rate is configured to be equal to the quotient of the sampling rate divided by the buffering rate, and
wherein the buffering rate and the sampling rate are configured such that the spectral interference caused by the sleep cycle rate occurs in the sampled signal at the one or more frequencies that are outside of the target frequency band of the sampled signal.

34. The method of claim 33, wherein the buffering rate and the sampling rate are configured such that the sleep cycle rate is greater than an upper bound frequency of the target frequency band of the sampled signal or less than a lower bound frequency of the target frequency band of the sampled signal.

35. The method of claim 25,
wherein the analog-to-digital converter is a first analog-to-digital converter, wherein the input signal is a first input signal, wherein the sampled signal is a first sampled signal,
wherein the method further comprises:
sampling, with a second analog-to-digital converter, a second input signal at a sampling rate to produce a second sampled signal;
buffering, with the processor, the second sampled signal at a buffering rate, the buffering rate being indicative of a number of data samples to buffer per invocation of a processing algorithm; and
invoking, with the processor, instances of the processing algorithm at a rate equal to a quotient of the sampling rate divided by the buffering rate to process the second sampled signal,
wherein the sleep cycle rate is configured to be equal to the quotient of the sampling rate divided by the buffering rate, and
wherein the buffering rate and the sampling rate are configured such that the spectral interference caused by the sleep cycle rate occurs in the first sampled signal at the one or more frequencies that are outside of the target frequency band of the first sampled signal.

36. The method of claim 35, wherein the buffering rate and the sampling rate are configured such that the sleep cycle rate is greater than an upper bound frequency of the target frequency band of the first sampled signal or less than a lower bound frequency of the target frequency band of the first sampled signal.

37. The method of claim 25, further comprising:
invoking, with the processor, instances of a processing algorithm at an algorithm processing rate to process the sampled signal,
for each of the instances of the processing algorithm that are invoked, executing, with the processor, the respective instance of the processing algorithm during a number of separate time intervals, each of the separate time intervals being separated from adjacent time intervals by a time interval where the respective processing algorithm is not executed, the number of separate time intervals being determined by an algorithm subdivision factor,
wherein the sleep cycle rate is configured to be equal to a product of an algorithm processing rate and the algorithm subdivision factor, and
wherein the algorithm processing rate and the algorithm subdivision factor are configured such that the spectral interference caused by the sleep cycle rate occurs in the sampled signal at the one or more frequencies that are outside of the target frequency band of the sampled signal.

38. The method of claim 37, wherein the algorithm processing rate and the algorithm subdivision factor are configured such that the sleep cycle rate is greater than an upper bound frequency of the target frequency band of the sampled signal or less than a lower bound frequency of the target frequency band of the sampled signal.

39. The method of claim 37,
wherein sampling, with the analog-to-digital converter, the input signal comprises sampling the input signal at a sampling rate to produce the sampled signal,
wherein the method further comprises buffering, with the processor, the sampled signal at a buffering rate, the buffering rate being indicative of a number of data samples to buffer per invocation of the processing algorithm,
wherein the algorithm processing rate is equal to a quotient of the sampling rate divided by the buffering rate,
wherein the sampling rate, the buffering rate and the algorithm subdivision factor are configured such that the spectral interference caused by the sleep cycle rate occurs in the sampled signal at the one or more frequencies that are outside of the target frequency band of the sampled signal.

40. The method of claim 25,
wherein the analog-to-digital converter is a first analog-to-digital converter, wherein the input signal is a first input signal, wherein the sampled signal is a first sampled signal,
wherein the method further comprises:
sampling, with a second analog-to-digital converter, a second input signal to produce a second sampled signal;
invoking, with the processor, instances of a processing algorithm at an algorithm processing rate to process the second sampled signal;
for each of the instances of the processing algorithm that are invoked, executing, with the processor, the respective instance of the processing algorithm during a number of separate time intervals, each of the separate time intervals being separated from adjacent time intervals by a time interval where the respective processing algorithm is not executed, the number of separate time intervals being determined by an algorithm subdivision factor,
wherein the sleep cycle rate is configured to be equal to a product of the algorithm processing rate and the algorithm subdivision factor, and
wherein the algorithm processing rate and the algorithm subdivision factor are configured such that the spectral interference caused by the sleep cycle rate occurs in the first sampled signal at the one or more frequencies that are outside of the target frequency band of the first sampled signal.

41. The method of claim 40, wherein the algorithm processing rate and the algorithm subdivision factor are configured such that the sleep cycle rate is greater than an upper bound frequency of the target frequency band of the first sampled signal or less than a lower bound frequency of the target frequency band of the first sampled signal.

42. The method of claim 40,
wherein sampling, with the second analog-to-digital converter, the second input signal comprises sampling the second input signal at a sampling rate to produce the second sampled signal,
wherein the method further comprises buffering the second sampled signal at a buffering rate, the buffering rate being indicative of a number of data samples to buffer per invocation of the processing algorithm,
wherein the algorithm processing rate is equal to a quotient of the sampling rate divided by the buffering rate, and
wherein the sampling rate, the buffering rate and the algorithm subdivision factor are configured such that the spectral interference caused by the sleep cycle rate occurs in the first sampled signal at the one or more frequencies that are outside of the target frequency band of the first sampled signal.

43. The method of claim 25, wherein the physiological signal is brain signal and the target frequency band is one of an alpha, beta, gamma or fast ripple frequency band of the brain signal.

44. The method of claim 43, wherein the brain signal comprises at least one of an electroencephalogram (EEG) signal, an electrocorticogram (ECoG) signal, a local field potential (LFP) signal, or a single cell action potential signal.

45. The method of claim 25, further comprising determining, with the processor, at least one of a power level of the target frequency band in the sampled signal and a power fluctuation of the target frequency band in the sampled signal.

46. The method of claim 25, further comprising analyzing, with the processor, the target frequency band of the sampled signal.

47. The method of claim 25, wherein the target frequency band of the sampled signal is a target frequency band to be analyzed during post-processing of the sampled signal.

48. The method of claim 25, wherein the power source, the power distribution network, the analog-to-digital converter, and the processor are included in an implantable medical device.

49. An apparatus for monitoring signals comprising:
means for sampling an input signal to produce a sampled signal; and
means for cycling between an algorithm processing mode and a sleep mode based on a sleep cycle rate,
wherein the means for sampling and the means for cycling are electrically coupled to a power distribution network that is electrically coupled to a power source,
wherein the sleep cycle rate causes spectral interference to propagate through the power distribution network and into the sampled signal, and
wherein the sleep cycle rate further causes the spectral interference that is generated due to the sleep cycle rate to occur in the sampled signal at one or more frequencies that are outside of a target frequency band of the sampled signal.

* * * * *

UNITED STATES PATENT AND TRADEMARK OFFICE
CERTIFICATE OF CORRECTION

PATENT NO. : 9,439,150 B2  Page 1 of 1
APPLICATION NO. : 13/862227
DATED : September 6, 2016
INVENTOR(S) : Carlson et al.

It is certified that error appears in the above-identified patent and that said Letters Patent is hereby corrected as shown below:

On the Title Page (54): "PHYSIOLOGICAL SIGNAL MONTORING" should read --PHYSIOLOGICAL SIGNAL MONITORING--

Signed and Sealed this
Fifth Day of June, 2018

Andrei Iancu
*Director of the United States Patent and Trademark Office*